United States Patent
Aguirre-Valencia

(10) Patent No.: US 9,956,054 B2
(45) Date of Patent: May 1, 2018

(54) DYNAMIC MINIMALLY INVASIVE SURGICAL-AWARE ASSISTANT

(71) Applicant: EchoPixel, Inc., Los Altos Hills, CA (US)

(72) Inventor: Sergio Aguirre-Valencia, Santa Clara, CA (US)

(73) Assignee: EchoPixel, Inc., Los Altos Hills, CA (US)

( * ) Notice: Subject to any disclaimer, the term of this patent is extended or adjusted under 35 U.S.C. 154(b) by 161 days.

(21) Appl. No.: 15/192,853

(22) Filed: Jun. 24, 2016

(65) Prior Publication Data

US 2016/0381256 A1 Dec. 29, 2016

Related U.S. Application Data

(60) Provisional application No. 62/231,150, filed on Jun. 25, 2015.

(51) Int. Cl.
| | |
|---|---|
| *A61B 90/00* | (2016.01) |
| *H04N 13/00* | (2018.01) |
| *G06F 3/147* | (2006.01) |
| *A61B 34/20* | (2016.01) |
| *A61B 34/00* | (2016.01) |

(Continued)

(52) U.S. Cl.
CPC ............ *A61B 90/37* (2016.02); *A61B 34/20* (2016.02); *A61B 34/25* (2016.02); *G06F 3/147* (2013.01); *H04N 13/004* (2013.01); *H04N 13/02* (2013.01); *H04N 13/04* (2013.01); *A61B 2034/2055* (2016.02); *A61B 2034/2065* (2016.02); *A61B 2034/252* (2016.02); *G09G 2340/0407* (2013.01); *G09G 2340/0464* (2013.01); *H04N 2201/0079* (2013.01)

(58) Field of Classification Search
CPC ......... A61B 90/37; A61B 34/20; A61B 34/25; A61B 2034/2055; A61B 2034/2065; A61B 2034/252; G06F 3/147; H04N 13/0004; H04N 13/02; H04N 13/04; H04N 2201/0079; G09G 2340/0407; G09G 2340/0464
See application file for complete search history.

(56) References Cited

U.S. PATENT DOCUMENTS

| | | | |
|---|---|---|---|
| 2004/0047044 A1* | 3/2004 | Dalton ................... | A61B 6/462 359/630 |
| 2004/0171924 A1* | 9/2004 | Mire ...................... | A61B 34/20 600/407 |
| 2008/0013809 A1* | 1/2008 | Zhu ....................... | G06F 19/321 382/128 |

* cited by examiner

*Primary Examiner* — Michael Teitelbaum
(74) *Attorney, Agent, or Firm* — Steven Stupp

(57) ABSTRACT

A computer system that provides situational awareness and feedback during a surgical procedure is described. During operation, the computer system generates stereoscopic images at a first 3-dimensional (3D) location in an individual, where the stereoscopic images include image parallax and are based on data having a discrete spatial resolution and a predefined surgical plan for the individual. Then, the computer system provides the stereoscopic images to a display. When a surgical tool is advanced, location information of the surgical tool is updated in the stereoscopic images displayed are updated. Alternatively or additionally, When location information indicates a deviation from the predefined surgical plan during the surgical procedure, the computer system generates revised stereoscopic images that indicate: the deviation has occurred an update to the predefined surgical plan and/or how to return to the predefined surgical plan.

20 Claims, 21 Drawing Sheets

(51) Int. Cl.
*H04N 13/02* (2006.01)
*H04N 13/04* (2006.01)

DYNAMIC MINIMALLY INVASIVE SURGICAL-AWARE ASSISTANT

CROSS REFERENCE TO RELATED APPLICATION

This application claims priority under 35 U.S.C. 119(e) to U.S. Provisional Application Ser. No. 62/231,150, entitled "Dynamic Minimally Invasive Surgical-Awareness Assistant," by Sergio Aguirre-Valencia, filed on Jun. 25, 2016, the contents of which are herein incorporated by reference.

BACKGROUND

Field

The described embodiments relate to techniques for presenting three-dimensional information.

Related Art

Many electronic devices include display subsystems that use image-rendering techniques to present visual information to users. For example, many existing display subsystems present visual information using one or more two-dimensional (2D) images (such as a 2D view of an image in a plane) that are displayed on a display.

However, it can be difficult to accurately present three-dimensional (3D) information to the users using 2D images. For example, in many computer-vision applications, a 2D image or a sequence of 2D images (which is sometimes referred to as '2.5D' images) based on an extracted surface or a volume rendering is often used to specify a single 3D-perspective view projected on to a plane, thereby simulating the appearance of 3D information. Nonetheless, the 2.5D images are not typically 3D images. In particular, the 2.5D images do not include image parallax (i.e., they do not provide stereoscopic viewing based on the offset between the left and right eyes of a viewer). Therefore, the 3D-perspective view provided by 2.5D images may not be the same as that provided by an actual 3D image. The differences that occur can result in distortions, which can degrade the accuracy of the viewer's perception of the presented 3D information (which can result in errors) and may degrade the viewer experience by making it more difficult, time consuming and tiring for the viewer to look at the 3D information.

SUMMARY

The described embodiments include a computer system that provides situational awareness and feedback during a surgical procedure, such as a minimally invasive surgical procedure. During operation, the computer system generates stereoscopic images at a first 3-dimensional (3D) location in an individual, where the stereoscopic images include image parallax, and where the stereoscopic images correspond to a first viewing plane and are based on data having a discrete spatial resolution and a predefined surgical plan for the individual from preoperative and/or intraoperative images. Then, the computer system provides the stereoscopic images to a display. Moreover, the computer system receives location information of one or more surgical tools as they are being advanced or positioned in the patient. Then, the computer system generates second stereoscopic images at a second 3D location in the individual, where the second stereoscopic images include image parallax and motion parallax relative to the stereoscopic images, and where the second stereoscopic images correspond to a second viewing plane and are based on the data having the discrete spatial resolution and the predefined surgical plan for the individual. Then, the computer system provides the second stereoscopic images to the display. Next, the computer system receives second location information that indicates a deviation from the predefined surgical plan during the surgical procedure. Furthermore, the computer system generates third stereoscopic images at a third 3D location in the individual, where the third stereoscopic images include image parallax and motion parallax relative to the second stereoscopic images, and where the third stereoscopic images correspond to a third viewing plane and are based on the data having the discrete spatial resolution and the predefined surgical plan for the individual. Additionally, the computer system provides the third stereoscopic images to the display.

Note that the third stereoscopic images may: indicate that the deviation has occurred; update the predefined surgical plan into a new surgical plan; and/or indicate how to return to the predefined surgical plan.

Moreover, the computer system may include the display. Furthermore, providing the stereoscopic images, the second stereoscopic images and/or the third stereoscopic images may involve displaying the stereoscopic images, the second stereoscopic images and/or the third stereoscopic images on the display.

Note that the location information and/or the second location information may track the position of the one or more surgical tools in the individual using a 3D local positioning system.

Moreover, the location information and/or the second location information may track the progression of treatment across multiple interventions.

Furthermore, the second viewing plane and the third viewing plane may overlap with the first viewing plane to provide the stereoscopic images in a common frame of reference.

Another embodiment provides a computer-program product for use with the computer system. This computer-program product includes instructions for at least some of the operations performed by the computer system.

Another embodiment provides a method, which may be performed by the computer system. During the method, the computer system may perform at least some of the operations described above.

Figure 1:
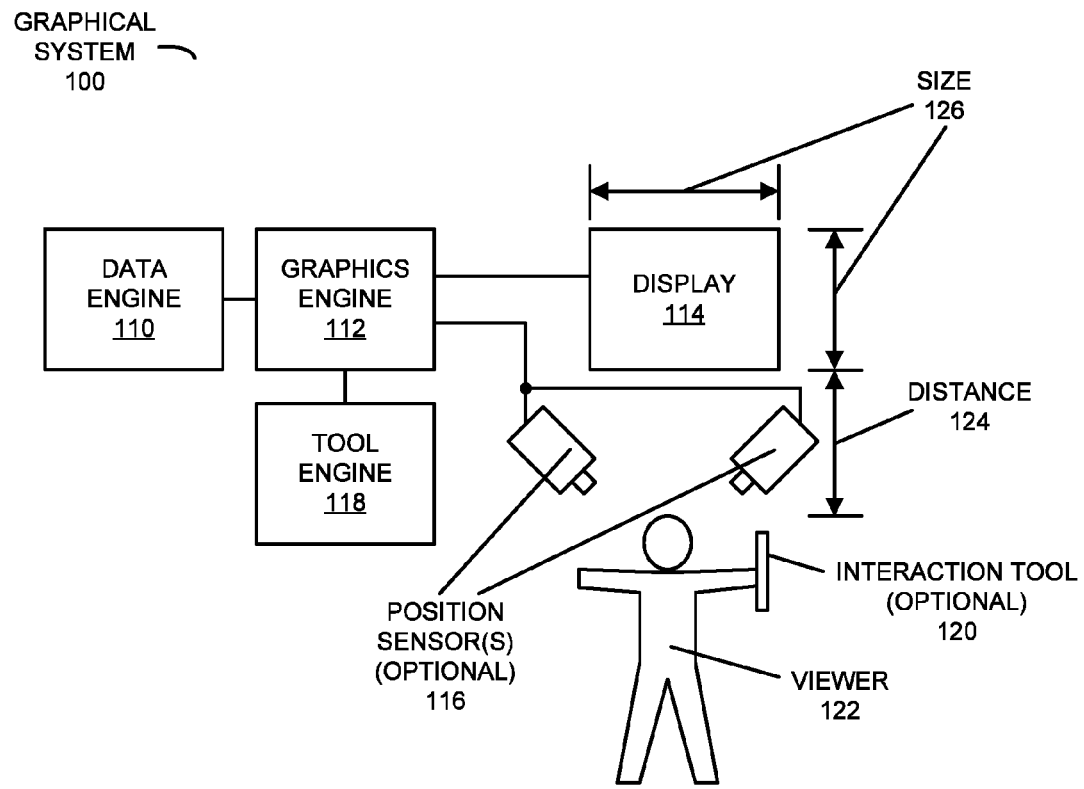
FIG. 1 is a block diagram illustrating a graphical system in accordance with an embodiment of the present disclosure.

Table 1 provides pseudo-code for a segmentation calculation at the interface between tissue classes in accordance with an embodiment of the present disclosure.

Table 2 provides a tree-structured articulated model of anatomical segments in accordance with an embodiment of the present disclosure.

Table 3 provides pseudo-code for a tree-structured articulated model of anatomical segments in accordance with an embodiment of the present disclosure.

Table 4 provides a representation of a problem-solving virtual instrument in accordance with an embodiment of the present disclosure.

Table 5 provides pseudo-code for a segmentation calculation at the interface between tissue classes in virtual colonoscopy in accordance with an embodiment of the present disclosure.

Note that like reference numerals refer to corresponding parts throughout the drawings. Moreover, multiple instances of the same part are designated by a common prefix separated from an instance number by a dash.

DETAILED DESCRIPTION

Human perception of information about the surrounding environment contained in visible light (which is sometimes referred to as 'eyesight,' 'sight,' or 'vision') is facilitated by multiple physiological components in the human visual system, including senses that provide sensory inputs and the cognitive interpretation of the sensory inputs by the brain. The graphical system in the present application provides rendered images that intuitively facilitate accurate human perception of 3-dimensional (3D) visual information (i.e., the awareness of an object or a scene through physical sensation of the 3D visual information). In particular, the graphical system in the present application provides so-called True 3D via rendered left-eye and right-eye images that include apparent image parallax (i.e., a difference in the position of the object or the scene depicted in the rendered left-eye and the right-eye images that approximates the difference that would occur if the object or the scene were viewed along two different lines of sight associated with the positions of the left and right eyes). This apparent image parallax may provide depth acuity (the ability to resolve depth in detail) and thereby triggers realistic stereopsis in an individual (who is sometimes referred to as a 'user,' a 'viewer' or an 'observer'), i.e., the sense of depth (and, more generally, actual 3D information) that is perceived by the individual because of retinal disparity or the difference in the left and right retinal images that occur when the object or the scene is viewed with both eyes or stereoscopically (as opposed to viewing with one eye or monoscopically).

The True 3D provided by the graphical system may incorporate a variety of additional features to enhance or maximize the depth acuity. In particular, the depth acuity may be enhanced by scaling the objects depicted in left-eye and the right-eye images prior to rendering based on the spatial resolution of the presented 3D visual information and the viewing geometry. Moreover, the graphical system may include motion parallax (the apparent relative motion of a stationary object against a background when the individual moves) in a sequence of rendered left-eye and right-eye images so that the displayed visual information is modified based on changes in the position of the individual. This capability may be facilitated by a sensor input to the graphical system that determines or indicates the motion of the individual while the individual views the rendered left-eye and the right-eye images. Furthermore, the sequence of rendered left-eye and right-eye images may include prehension, which, in this context, is the perception by the individual of taking hold, seizing, grasping or, more generally, interacting with the object. This capability may be facilitated by another sensor input to the graphical system that monitors interaction between the individual and the displayed visual information. For example, the individual may interact with the object using a stylus. In addition, the depth acuity offered by the graphical system may be enhanced through the use of monoscopic depth cues, such as: relative sizes/positions (or geometric perspective), lighting, shading, occlusion, textural gradients, and/or depth cueing.

In a wide variety of applications, True 3D may allow the individual to combine cognition (i.e., a deliberative conscious mental process by which one achieves knowledge) and intuition (i.e., an unconscious mental process by which one acquires knowledge without inference or deliberative thought). This synergistic combination may further increase the individual's knowledge, allow them to use the graphical system to perform tasks more accurately and more efficiently. For example, this capability may allow a physician to synthesize the emotional function of the right brain with the analytical functions of the left brain to interpret the True 3D images as a more accurate and acceptable approximation of reality. In radiology, this may improve diagnoses or efficacy, and may increase the confidence of radiologists when making decisions. As a consequence, True 3D may allow radiologists to increase their throughput or workflow (e.g., the enhanced depth acuity may result in improved sensitivity to smaller features, thereby reducing the time needed to accurately resolve features in the rendered images). Alternatively, surgeons can use this capability to plan surgeries or to perform virtual surgeries (for example, to rehearse a surgery) which may otherwise be impossible using existing graphical systems. Furthermore, because the visual information in True 3D intuitively facilitates accurate human perception, it may be easier and less tiring for physicians to view the images provided by the graphical system than those provided by existing graphical systems. Collectively, these features may improve patient outcomes and may reduce the cost of providing medical care.

While the embodiments of True 3D may not result in perfect perception of the 3D visual information by all viewers (in principle, this may require additional sensory inputs, such as those related to balance), in general the deviations that occur may not be detected by most viewers. Thus, the graphical system may render images based on a volumetric virtual space that very closely approximates what the individual would see with their own visual system. As described further below in the discussion of applications of the graphical system, the deviations that do occur in the perception of the rendered images may be defined based on a given application, such as how accurately radiologists are able to detect the presence of cancer based on the images provided by the graphical system.

Graphical System

FIG. 1 presents a block diagram of a graphical system 100, including a data engine 110, graphics (or rendering) engine 112, display 114, one or more optional position sensor(s) 116, and tool engine 118. This graphical system may facilitate close-range stereoscopic viewing of 3D objects (such as those depicting human anatomy) with unrestricted head motion and hand-directed interaction with the 3D objects, thereby providing a rich holographic experience.

During operation, data engine 110 may receive input data (such as a computed-tomography or CT scan, histology, an ultrasound image, a magnetic resonance imaging or MRI scan, or another type of 2D image slice depicting volumetric information), including dimensions and spatial resolution. In an exemplary embodiment, the input data may include representations of human anatomy, such as input data that is compatible with a Digital Imaging and Communications in Medicine (DICOM) standard. However, a wide variety of types of input data may be used (including non-medical data), which may be obtained using different imaging techniques, different wavelengths of light (microwave, infrared, optical, x-ray), etc.

After receiving the input data, data engine 110 may: define segments in the data (such as labeling tissue versus air); other parameters (such as transfer functions for voxels); identify landmarks or reference objects in the data (such as anatomical features); and identify 3D objects in the data (such as the colon and, more generally, groups of voxels). One or more of these operations may be performed by or may be augmented based on input from a user or viewer 122 of graphical system 100.

As described further below, based on the information output by data engine 110 (including the left and right eye coordinates and distance 124 of viewer 122 from display 114), graphics engine 112 may define, for the identified 3D objects, model matrices (which specify where the objects are in space relative to viewer 122 using a model for each of the objects), view matrices (which specify, relative to a tracking camera in display 114, the location and/or gaze direction of the eyes of viewer 122), and projection or frustum matrices (which specify what is visible to the eyes of viewer 122). These model, view and frustum matrices may be used by graphics engine 112 to render images of the 3D objects. For a given eye, the rendered image may provide a 2.5D monoscopic projection view on display 114. By sequentially displaying left-eye and right-eye images that include image parallax (i.e., stereoscopic images), 3D information may be presented on display 114. These images may be appropriately scaled or sized so that the images match the physical parameters of the viewing geometry (including the position of viewer 122 and size 126 of the display 114). This may facilitate the holographic effect for viewer 122. In addition, the left-eye and the right-eye images may be displayed at a monoscopic frequency of at least 90 Hz (or a stereoscopic frequency of at least 45 Hz), which can be viewed by viewer 122 using polarized glasses. Note that this frequency may be large enough to avoid flicker even in ambient lighting and may be sufficient for viewer 122 to fuse the images to perceive stereopsis and motion.

Moreover, one or more optional position sensors 116 (which may be separate from or integrated into display 114) may dynamically track movement of the head of viewer 122 with up to six degrees of freedom, and this head-tracking information (e.g., the positions of the eyes of viewer 122 relative to display 114) may be used by graphics engine 112 to update the view and frustum matrices and, thus, the rendered left-eye and right-eye images. In this way, the rendered images may be optimal from the viewer perspective and may include motion parallax. In some embodiments, the one or more optional position sensor(s) 116 optionally dynamically track the gaze direction of viewer 122 (such as where viewer 122 is looking). By tracking where viewer 122 is looking, graphics engine 112 may include foveated imaging when rendering images, which can provide additional depth perception. For example, the transfer functions defined by data engine 110 may be used to modify the rendering of voxels in a 3D image (such as the transparency of the voxels) based on the focal plane of viewer 122.

Furthermore, tool engine 118 may dynamically track 3D interaction of viewer 122 with an optional physical interaction tool 120 (such as a stylus, a mouse or a touch pad that viewer 122 uses to interact with one or more of the displayed 3D objects) with up to six degrees of freedom. For example, viewer 122 can grasp an object and interact with it using optional interaction tool 120. The detected interaction information provided by tool engine 118 may be used by graphics engine 112 to update the view and frustum matrices and, thus, the rendered left-eye and right-eye images. In this way, the rendered images may update the perspective based on interaction of viewer 122 with one or more of the displayed 3D objects using the interaction tool (and, thus, may provide prehension), which may facilitate hand-eye coordination of viewer 122.

By using image parallax, motion parallax and prehension, graphical system 100 may provide cues that the human brain uses to understand the 3D world. In particular, the image parallax triggers stereopsis, while the motion parallax can enable the viewer to fuse stereoscopic images with greater depth. In addition, the kinesthetic (sensory) input associated with the prehension in conjunction with the stereopsis may provide an intuitive feedback loop between the mind, eyes and hand of viewer 122 (i.e., the rich holographic experience).

Note that the one or more optional position sensors 116 may use a wide variety of techniques to track the locations of the eyes of viewer 122 and/or where viewer 122 is looking (such as a general direction relative to display 114). For example, viewer 122 may be provided glasses with reflecting surfaces (such as five reflecting surfaces), and infrared light reflected off of these surfaces may be captured by cameras or imaging sensors (which may be integrated into or included in display 114). This may allow the 3D coordinates of the reflecting surfaces to be determined. In turn, these 3D coordinates may specify the location and/or the viewing direction of the eyes of viewer 122, and can be used to track head movement. Alternatively or additionally, stereoscopic triangulation may be used, such as Leap (from Leap Motion, Inc. of San Francisco, Calif.). For example, two (left/right) camera views of the face of viewer 122 may be used to estimate what viewer 122 is looking at. In particular, image processing of the two camera views may allow the 3D coordinates of the eyes of viewer 122 to be determined. Another technique for tracking head motion may include sensors (such as magnetic sensors) in the glasses that allow the position of the glasses to be tracked. More generally, a gyroscope, electromagnetic tracking (such as that offered by Northern Digital, Inc. of Ontario, Canada), a local positioning system and/or a time of flight technique may be used to track the head position of viewer 122, such as Kinect (from Microsoft Corporation of Redmond, Wash.). In the discussion that follows, cameras in display 114 are used as an illustrative example of a technique for tracking the location and/or gaze direction of the eyes of viewer 122.

Furthermore, instead of optional physical interaction tool 120, in some embodiments viewer 122 may interact with displayed objects by using gestures in space (such as by moving one or more fingers on one or more of their hands). For example, a time of flight technique may be used (such as Kinect) and/or stereoscopic triangulation may be used (such as Leap). More generally, the position or motion of optional physical interaction tool 120 may be determined: optically, using magnetic sensors, using electromagnetic tracking, using a gyroscope, using stereoscopic triangulation and/or using a local positioning system.

Note that optional physical interaction tool 120 may provide improved spatial control for viewer 122 (such as a surgeon) when interacting with the displayed objects.

Additionally, a wide variety of displays and display technologies may be used for display 114. In an exemplary embodiment, display 114 integrates the one or more optional position sensors 116. For example, display 114 may be provided by Infinite Z, Inc. (of Mountain View, Calif.) or Leonar3do International, Inc. (of Herceghalom, Hungary). Display 114 may include: a cathode ray tube, a liquid crystal display, a plasma display, a projection display, a holographic display, an organic light-emitting-diode display, an electronic paper display, a ferroelectric liquid display, a flexible display, a head-mounted display, a retinal scan display, and/or another type of display. In an exemplary embodiment, display 114 is a 2D display. However, in embodiments where display includes a holographic display, instead of sequentially (and alternately) displaying left-eye and right-eye images, at a given time a given pair of images (left-eye and right-eye) may concurrently displayed by display 114 or the information in the given pair of images may be concurrently displayed by display 114. Thus, display 114 may be able to display magnitude and/or phase information.

Image Processing and Rendering Operations

Graphical engine 112 may implement a vertex-graphics-rendering process in which 3D vertices define the corners or intersections of voxels and, more generally, geometric shapes in the input data. In an exemplary embodiment, graphics engine 112 uses a right-handed coordinate system. Graphics engine 112 may use physical inputs (such as the position of the eyes of viewer 122) and predefined parameters (such as those describing size 126 of display 114 in FIG. 1 and the viewing geometry) to define the virtual space based on matrices. Note that graphics engine 112 'returns' to the physical space when the left-eye and right-eye images are rendered based on the matrices in the virtual space.

In the virtual space, 3D objects may each be represented by a 4×4 matrix with an origin position, a scale and an orientation. These objects may depict images, 3D volumes, 3D surfaces, meshes, lines or points in the input data. For computational simplicity, all the vertices may be treated as three-dimensional homogeneous vertices that include four coordinates, three geometric coordinates (x, y, and z) and a scale w. These four coordinates may define a 4×1 column vector $(x, y, z, w)^T$. Note that: if w equals one, then the vector (x, y, z, 1) is a position in space; if w equals zero, then the vector (x, y, z, 0) is a position in a direction; and if w is greater than zero, then the homogeneous vertex $(x, y, z, w)^T$ corresponds to the 3D point $(x/w, y/w, z/w)^T$.

Using homogeneous coordinates, a vertex array can represent a 3D object. In particular, an object matrix M may initially be represented as $$\begin{bmatrix} m0 & m4 & m8 & m12 \\ m1 & m5 & m9 & m13 \\ m2 & m6 & m10 & m14 \\ m3 & m7 & m11 & m15 \end{bmatrix},$$

where, by default, (m0, m1, m2) may be the +x axis (left) vector (1, 0, 0), (m4, m5, m6) may be the +y axis (up) vector (0, 1, 0), (m8, m9, m10) may be the +z axis (forward) vector (0, 0, 1), m3, m7, and m11 may define the relative scale of these vectors along these axes, m12, m13, m14 specify the position of a camera that tracks the positions of the eyes of viewer 122, and m15 may be one.

By applying a rotation operation (R), a translation operation (T) and a scaling operation (S) across the vertex array of an object (i.e., to all of its (x, y, z, w) vectors), the object can be modified in the virtual space. For example, these operations may be used to change the position of the object based on where viewer 122 is looking, and to modify the dimensions or scale of the object so that the size and proportions of the object are accurate. In particular, a transformed vector may be determined using $$S \cdot R \cdot T \cdot I_0,$$

where $I_0$ is an initial vector in the virtual space. Note that, in a right-handed coordinate system, a rotation a about the x axis (Rx), a rotation a about the y axis (Ry) and a rotation a about the z axis (Rz), respectively, can be represented as $$Rx = \begin{bmatrix} 1 & 0 & 0 & 0 \\ 0 & \cos(a) & -\sin(a) & 0 \\ 0 & \sin(a) & \cos(a) & 0 \\ 0 & 0 & 0 & 1 \end{bmatrix},$$

$$Ry = \begin{bmatrix} \cos(a) & 0 & \sin(a) & 0 \\ 0 & 1 & 0 & 0 \\ -\sin(a) & 0 & \cos(a) & 0 \\ 0 & 0 & 0 & 1 \end{bmatrix}$$

and $$Rz = \begin{bmatrix} \cos(a) & -\sin(a) & 0 & 0 \\ \sin(a) & \cos(a) & 0 & 0 \\ 0 & 0 & 1 & 0 \\ 0 & 0 & 0 & 1 \end{bmatrix}.$$

Similarly, a translation by (x, y, z) can be represented as $$T = \begin{bmatrix} 1 & 0 & 0 & x \\ 0 & 1 & 0 & y \\ 0 & 0 & 1 & z \\ 0 & 0 & 0 & 1 \end{bmatrix},$$

a non-uniform scaling by $s_x$ along the x axis, $s_y$ along the y axis and $s_z$ along the z axis can be represented as $$S = \begin{bmatrix} s_x & 0 & 0 & 0 \\ 0 & s_y & 0 & 0 \\ 0 & 0 & s_z & 0 \\ 0 & 0 & 0 & 1 \end{bmatrix}$$

and a uniform scaling s can be represented as $$S = \begin{bmatrix} 1 & 0 & 0 & 0 \\ 0 & 1 & 0 & 0 \\ 0 & 0 & 1 & 0 \\ 0 & 0 & 0 & s \end{bmatrix}.$$

Moreover, note that an arbitrary combination of rotation, translation and scaling matrices is sometimes referred to as a 'transformation matrix' Tf. Therefore, after applying the rotation, translation and scaling matrices, the model matrix M may become a model transformation matrix Mt. This transformation matrix may include the position of the object $(tx, ty, tz, 1)^T$, the scale s of the object and/or the direction R of the object $[(r1, r2, r3)^T, (r4, r5, r6)^T, (r7, r8, r9)^T]$. Thus, the transformation matrix Mt may be generated by: translating the object to its origin position $(tx, ty, tz, 1)^T$; rotating the object by R; and/or scaling the object by s. For example, with uniform scaling the transformation matrix Mt may be represented as $$\begin{bmatrix} r1 & r4 & r7 & tx \\ r2 & r5 & r8 & ty \\ r3 & r6 & r9 & tz \\ 0 & 0 & 0 & s \end{bmatrix}.$$

In addition to the model matrices for the objects, graphics engine 112 may also implement so-called 'views' and 'perspective projections,' which may each be represented using homogeneous 4×4 matrices. The view may specify the position and/or viewing target (or gaze direction) of viewer 122 (and, thus, may specify where the objects are in space relative to viewer 122). In the virtual space, a given view matrix V (for the left eye or the right eye) may be based on the position of a camera that tracks the positions of the eyes of viewer 122, the location the camera is targeting, and the direction of the unit vectors (i.e., which way is up), for example, using a right-hand coordinate system. In the physical space, the view matrices V may be further based on the eye positions of viewer 122, the direction of the unit vectors and/or where viewer 122 is looking. In an exemplary embodiment, the view matrices V are created by specifying the position of the camera and the eyes of viewer 122, specifying the target coordinate of the camera and the target coordinate of the eyes of viewer 122, and a vector specifying the normalized +y axis (which may be the 'up' direction in a right-handed coordinate system). For example, the target coordinate may be the location that the camera (or the eyes of viewer 122) is pointed, such as the center of display 114.

In an exemplary embodiment, the given view matrix V is determined by constructing a rotation matrix Rv. In this rotation matrix, the 'z axis' may be defined as the normal from given camera position $(px, py, pz)^T$ minus the target position, i.e., $(z1,z2,z3)^T = \text{normal}[(px,py,pz)^T - (tx,ty,tz)^T].$ Then, the 'x axis' may be calculated as the normal of the cross product of the 'z axis' and normalized +y axis (which may represent the 'up' direction), i.e., $(x1, x2, x3)^T = \text{normal}[\text{crosss}[(z1,z2,z3)^T, (ux,uy,uz)^T]].$ Moreover, the un-normalized y axis may be calculated as the cross product of the 'z axis' and 'x axis,' i.e., $(y1, y2, y3)^T = \text{normal}[(z1, z2,z3)^T, (x1, x2, x3)^T].$ Thus, the complete 4×4 rotation matrix Rv for use in determining the given view matrix may be $$\begin{bmatrix} x1 & y1 & z1 & 0 \\ x2 & y2 & z2 & 0 \\ x3 & y3 & z3 & 0 \\ 0 & 0 & 0 & 1 \end{bmatrix}.$$

Next, the given view matrix V may also be determined by constructing a translation matrix Tv based on the position of one of the eyes of viewer 122 (tx, ty, tz). In particular, the translation matrix Tv may be represented as $$Tv = \begin{bmatrix} 1 & 0 & 0 & tx \\ 0 & 1 & 0 & ty \\ 0 & 0 & 1 & tx \\ 0 & 0 & 0 & 1 \end{bmatrix}.$$

Using the rotation matrix Rv and the translation matrix Tv, the inverse of the given view matrix $V^{-1}$ may be determined as $V^{-1} = Rv \cdot Tv$ or $$V^{-1} = \begin{bmatrix} x1 & y1 & z1 & tx \\ x2 & y2 & z2 & ty \\ x3 & y3 & z3 & tz \\ 0 & 0 & 0 & 1 \end{bmatrix}.$$

The perspective projection may use left-eye and right-eye frustums F to define how the view volume is projected on to a 2-dimensional (2D) plane (e.g., the viewing plane, such as display 114) and on to the eyes of viewer 122 (which may specify what is visible to the eyes of viewer 122). In the virtual space, a given frustum (for the left eye or the right eye) may be the portion of the 3D space (and the 3D objects it contains) that may appear or be projected as 2D left-eye or right-eye images on display 114. In the physical space, the given frustum may be the viewing volume that defines how the 3D objects are projected on to one of the eyes of viewer 122 to produce retinal images of the 3D objects that will be perceived (i.e., the given frustum specifies what one of the eyes of viewer 122 sees or observes when viewing display 114). Note that the perspective projection may project all points into a single point (an eye of viewer 122). As a consequence, the two perspective projections, one for the left eye of the viewer and another for the right eye of the viewer, are respectively used by graphics engine 112 when determining the left-eye image and the right-eye image. In general, for an arbitrary head position of viewer 122, the projection matrices or frustums for the left eye and the right eye are different from each other and are asymmetric.

Figure 2:
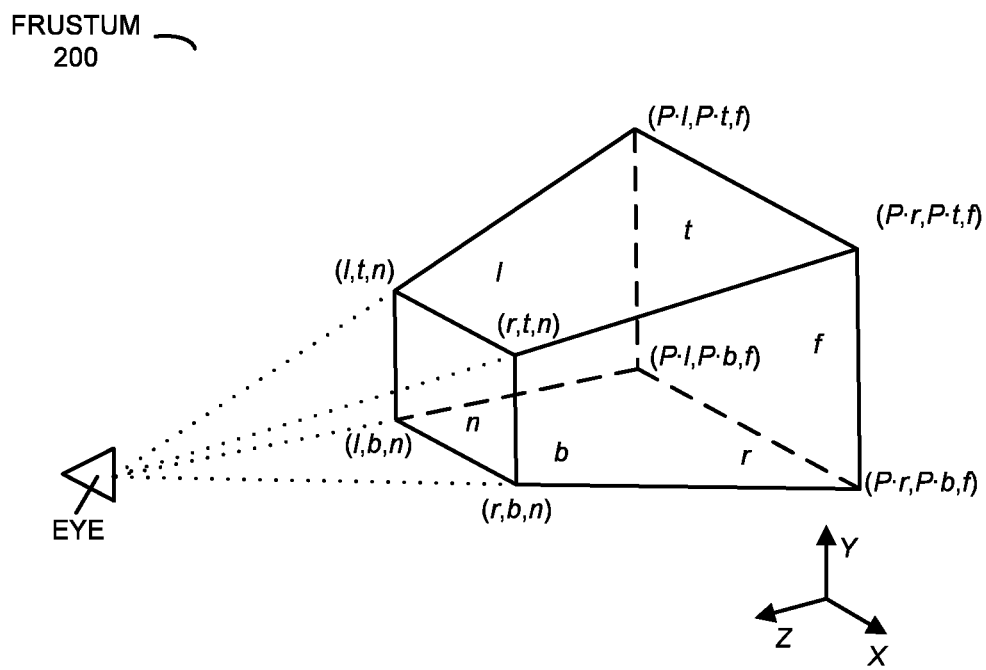
FIG. 2 is a drawing illustrating a frustum for a vertical display in the graphical system of FIG. 1 in accordance with an embodiment of the present disclosure.

FIG. 2 presents a drawing illustrating a frustum 200 for a vertical display in graphical system 100. This frustum includes: a near plane (or surface), a far (or back) plane, a left plane, a right plane, a top plane and a bottom plane. In this example, the near plane is defined at z equal to n. Moreover, the vertices of the near plane are at x equal to l and r (for, respectively, the left and right planes) and y equal to t and b (for, respectively, the top and bottom planes). The vertices of the far f plane can be calculated based on the ratio of similar triangles as $$\frac{f}{n} = \frac{left_{far}}{l} = \frac{l_{far}}{l},$$

which can be re-arranged as $$l_{far} = \left(\frac{f}{n}\right) \cdot l.$$

By defining a perspective projection factor P as $$\frac{f}{n}$$

this can be re-expressed as $$l_{far} = P \cdot l.$$

As shown in FIG. 2, the coordinates of the vertices at the far plane in frustum 200 can be expressed in terms of the coordinates at the near plane and the perspective projection factor P. Moreover, frustum (F) 200 can be expressed as a 4×4 matrix $$F = \begin{bmatrix} \frac{2n}{r-l} & 0 & \frac{r+l}{r-l} & 0 \\ 0 & \frac{2n}{t-b} & \frac{t+b}{t-b} & 0 \\ 0 & 0 & \frac{-(f+n)}{f-n} & \frac{-2fn}{f-n} \\ 0 & 0 & -1 & 0 \end{bmatrix}.$$

In an exemplary embodiment, when the head position of viewer 122 in FIG. 1 is not tracked (i.e., when motion parallax is not included), the near plane may be coincident with display 114 in FIG. 1. (In the discussion that follows, the plane of display 114 in FIG. 1 is sometimes referred to as the 'viewing plane.') In this case, frustum 200 extends behind the plane of display 114 (FIG. 1). Because viewer perception of stereopsis is high between 15 and 65 cm, and eventually decays at larger distances away from viewer 122 (FIG. 1), the far plane may define a practical limit to the number of vertices that are computed by graphics engine 112 (FIG. 1). For example, f may be twice n. In addition, as described further below, by defining a finite space, the left-eye and right-eye images may be scaled to enhance or maximize the depth acuity resolved by viewer 122 (FIG. 1) for a given spatial resolution in the input data and the viewing geometry in graphical system 100 in FIG. 1 (which is sometimes referred to as 'stereopsis scaling' or 'stereo-acuity scaling').

Figure 3:
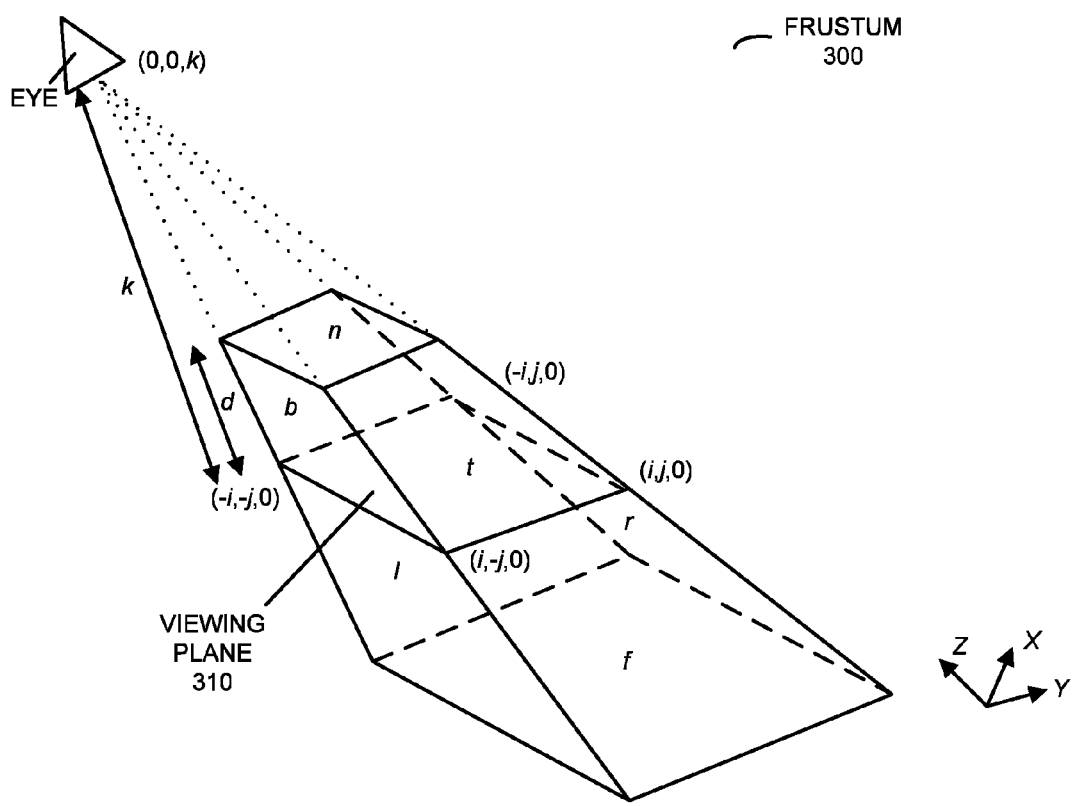
FIG. 3 is a drawing illustrating a frustum for a horizontal display in the graphical system of FIG. 1 in accordance with an embodiment of the present disclosure.
Figure 4:
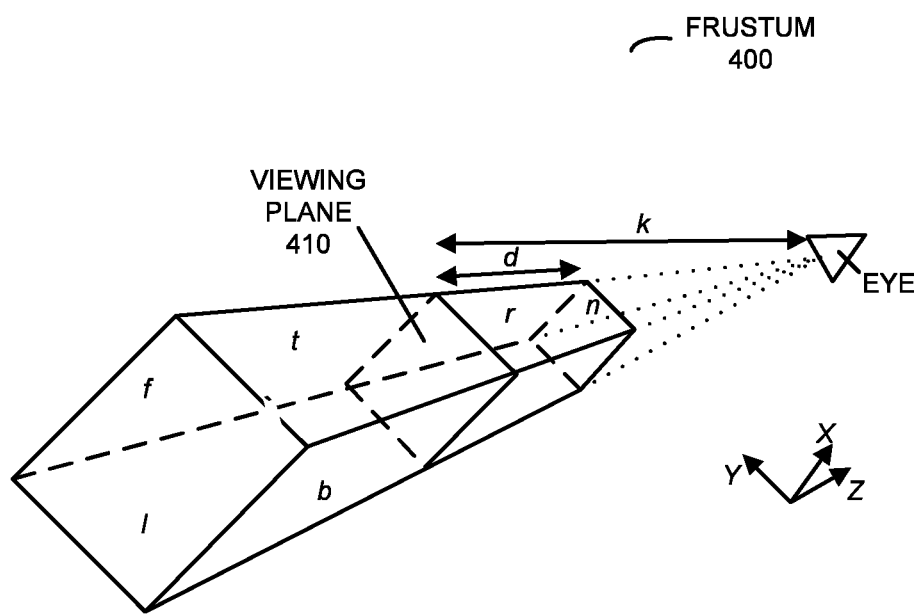
FIG. 4 is a drawing illustrating a frustum for an inclined display in the graphical system of FIG. 1 in accordance with an embodiment of the present disclosure.

While the preceding example of the frustum used a vertical display, in other embodiments display 114 (FIG. 1) may be horizontal or may be at an incline. For example, in surgical applications, display 114 (FIG. 1) may be placed on the floor. As shown in FIGS. 3 and 4, which present drawings illustrating frustums 300 (FIGS. 3) and 400, in these configurations the frustums are rotated.

When the position of the head or the eyes of viewer 122 (FIG. 1) are tracked in graphical system 100 in FIG. 1 (so that the rendered left-eye and right-eye images can be modified accordingly), the viewing plane may be placed approximately in the middle of the frustums to provide back-and-forth spatial margin. This is illustrated by viewing planes 310 (FIGS. 3) and 410. Moreover, as shown in FIG. 3, the coordinates of the vertices of viewing plane 310 may be left (−i), right (+i), top (+j), bottom (−j), and the z (depth) coordinate may be zero so that the near plane is at z coordinate d and the eyes of viewer 122 (FIG. 1) are at z coordinate k. (In some embodiments, the near plane is defined at the same z coordinate as the eyes of viewer 122 in FIG. 1.) Based on these coordinates, the far-plane coordinates can be determined using the perspective projection factor P.

Note that, while the preceding example defined the frustum based on the distance z from viewer 122 (FIG. 1) to display 114 (FIG. 1), in embodiments where the one or more optional position sensors 116 (FIG. 1) track the gaze direction of viewer 122 (FIG. 1), the frustum may be based on the focal point of viewer (FIG. 1). Furthermore, while a viewing plane was used as a reference in the preceding discussion, in some embodiments multiple local planes (such as a set of tiled planes) at different distances z from viewer 122 (FIG. 1) to display 114 (FIG. 1) are used.

By multiplying the left-eye (or right-eye) frustum F by the corresponding left-eye (or right-eye) view matrix V and the model transformation matrix Mt, a 2D projection in the viewing plane of a 3D object can be determined for rendering as a given left-eye (or right-eye) image. These operations may be repeated for the other image to provide stereoscopic viewing. As described further below with reference to FIG. 6, note that when rendering these 2D projections, a surface may be extracted for a collection of voxels or a volume rending may be made based on ray tracing.

In order to enhance or maximize the depth acuity resolved by viewer 122 in FIG. 1 (and, thus, to provide high-resolution depth perception), the graphics engine 112 (FIG. 1) may ensure that the geometric disparity between the left-eye and the right-eye images remains between a minimum value that viewer 122 (FIG. 1) can perceive (which is computed below) and a maximum value (beyond which the human mind merges the left-eye and the right-eye images and stereopsis is not perceived). In principle, graphics engine 112 (FIG. 1) may scale the objects in the image(s) presented to viewer 122 (FIG. 1) in proportion to their focal distance z (which is sometimes referred to as a 'geometric perspective'), or may have free control of the focal distance of viewer 122 (FIG. 1) in order to accommodate all the objects viewer 122 (FIG. 1) wants to observe. The latter option is what happens in the real world. For example, when an individual focuses on a desk and, thus, has accommodated to a short focal distance, he or she can resolve depth with a precision of around 1 mm. However, when the individual is outside and accommodates to a longer focal distance, he or she can resolve depth with a precision of around 8 cm.

In practice, because graphical system 100 (FIG. 1) implements stereoscopic viewing (which provides depth information), it is not necessary to implement geometric perspective (although, in some embodiments, geometric perspective is used in graphical system 100 in FIG. 1 addition to image parallax). Instead, in graphical system 100 (FIG. 1) objects may be scaled in proportion to the distance z of viewer 122 (FIG. 1) from display 114 (FIG. 1). As described previously, a range of distances z may occur and, based on the head-tracking information, this range may be used to create the frustum. In particular, after determining the 2D projection, graphics engine 112 (FIG. 1) may scale a given object in the image(s) presented to the viewer based on based on the viewing geometry (including the distance z) and a given spatial resolution in the input data (such as the voxel spacing, the discrete spacing between image slices, and/or, more generally, the discrete spatial sampling in the input data) in order to enhance (and, ideally, to maximize or optimize) the depth acuity. This stereopsis scaling may allow viewer 122 (FIG. 1) to perceive depth information in the left-eye and the right-eye images more readily, and in less time and with less effort (or eye strain) for discretely sampled data. As such, the stereopsis scaling may significantly improve the viewer experience and may improve the ability of viewer 122 (FIG. 1) to perceive 3D information when viewing the left-eye and the right-eye images provided by graphical system 100 (FIG. 1).

Note that the stereopsis scaling may not be typically performed in computer-aided design systems because these approaches are often model-based which allows the resulting images to readily incorporate geometric perspective for an arbitrary-sized display. In addition, stereopsis scaling is typically not performed in 2.5D graphical systems because these approaches often include markers having a predefined size in the resulting images as comparative references.

Figure 5:
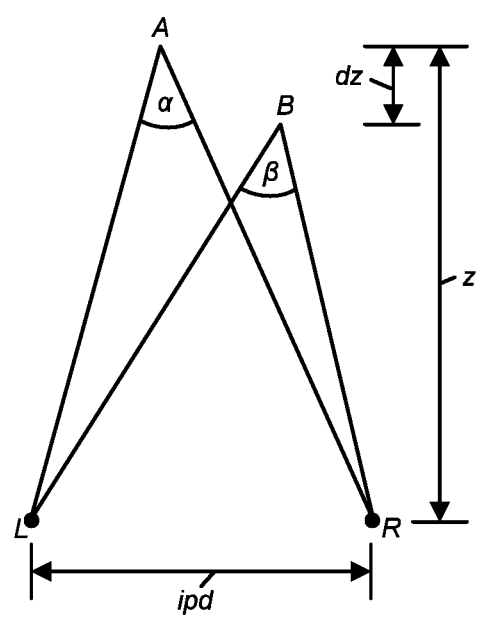
FIG. 5 is a drawing illustrating calculation of stereopsis scaling in the graphical system of FIG. 1 in accordance with an embodiment of the present disclosure.

FIG. 5 presents a drawing illustrating the calculation of the stereopsis scaling for a given spatial resolution in the input data and a given viewing geometry. In this drawing, ipd is the interpupillary distance, z is the distance to the focal point of viewer 122 (FIG. 1) (which, as noted previously, may be replaced by the distance between viewer 122 and display 114 in FIG. 1 in embodiments where the head position of viewer 122 is tracked), dz is the delta in the z (depth) position of an object to the focal point, L is the left eye-position and R is the right-eye position. Moreover, the geometric disparity $\delta y$ may be defined based on the difference in the angles $\alpha$ and $\beta$ times L, i.e., $$\delta\gamma = L \cdot (\alpha - \beta).$$

This can be re-expressed as $$\delta\gamma = \frac{(ipd) \cdot (dz)}{z^2 + z \cdot (dz)}.$$

If z is 400 mm, the ipd is 65 mm (on average) and dz is 1 mm, the geometric disparity $\delta\gamma$ equals $4.052 \times 10^{-4}$ radians or 82.506 arcseconds. As noted previously, viewers have minimum and maximum values of the geometric disparity $\delta\gamma$ that they can perceive. For a given distance z (which, as noted previously, may be determined by tracking the head position of viewer 122 in FIG. 1), the scale of the objects in the left-eye image and the right-eye image can be selected to enhance or maximize the depth acuity based on $$dz = \frac{\delta\gamma \cdot (z^2)}{ipd}, \quad (1)$$

which defines the minimum dz needed for stereopsis. For example, in the case of medical images, dz may be the voxel spacing. (Note that, for an x spacing dx, a y spacing dy and a z spacing dz, the voxel size dv may be defined as $$dv^2 = dx^2 + dy^2 + dz^2.)$$

Moreover, the minimum value of the geometric disparity Sy (which triggers stereopsis and defines the depth acuity) may be 2-10 arcseconds (which, for 10 arcseconds, is $4.486 \times 10^{-5}$ radians) and the maximum value may be 600 arcseconds (which, for 100 arcseconds, is $4.486 \times 10^{-4}$ radians). If the average distance z from the viewer to display 114 (FIG. 1) is 0.5 m (an extremum of the 0.5-1.5 m range over which the depth acuity is a linear function of distance z), the ipd equals 65 mm and the minimum value of the geometric disparity $\delta\gamma$ is 10 arcseconds, the minimum $dz_{min}$ in Eqn. 1 to maintain optimal depth acuity is 0.186 mm. Similarly, if the average distance z is 0.5 m, the ipd equals 65 mm and the maximum value of the geometric disparity $\delta\gamma$ is 100 arcseconds, the maximum $dz_{max}$ in Eqn. 1 to maintain optimal depth acuity is 1.86 mm. Defining the minimum scale $s_{min}$ as $$s_{min} = \frac{dz_{min}}{dv}$$

and the maximum scale $s_{max}$ as $$s_{max} = \frac{dz_{max}}{dv},$$

and for an isometric 1 mm voxel resolution, the minimum scale $s_{min}$ is 0.186 and the maximum scale $s_{max}$ is 1.86. Therefore, in this example the objects in left-eye and the right-eye images can be scaled by a factor between 0.186 and 1.86 (depending on the average tracked distance z) to optimize the depth acuity. Note that, in embodiments where the one or more optional position sensors 116 (FIG. 1) track the gaze direction of viewer 122 (FIG. 1), the stereopsis scaling may be varied based on the focal point of viewer 122 (FIG. 1) instead of the distance z from viewer 122 (FIG. 1) to display 114 (FIG. 1).

While the preceding example illustrated the stereopsis scaling based on an average $\delta\gamma$ and an average ipd, in some embodiments the stereopsis scaling is based on an individual's $\delta\gamma$ and/or ipd. For example, viewer 122 (FIG. 1) may provide either or both of these values to graphical system 100 (FIG. 1). Alternatively, graphical system 100 (FIG. 1) may measure the $\delta\gamma$ and/or the ipd of viewer 122 (FIG. 1). The stereopsis scaling is described further below with reference to FIG. 15.

Graphical system 100 (FIG. 1) may also implement monoscopic depth cues in the rendered left-eye and right-eye images. These monoscopic depth cues may provide a priori depth information based on the experience of viewer 122 (FIG. 1). Note that the monoscopic depth cues may complement the effect of image parallax and motion parallax in triggering stereopsis. In particular, the monoscopic depth cues may include: relative sizes/positions (or geometric perspective), lighting, shading, occlusion, textural gradients, and/or depth cueing.

As noted previously, a geometric-perspective monoscopic depth cue (which is sometimes referred to as a 'rectilinear perspective' or a 'photographic perspective') may be based on the experience of viewer 122 (FIG. 1) that the size of the image of an object projected by the lens of the eye onto the retina is larger when the object is closer and is smaller when the object is further away. This reduced visibility of distant object (for example, by expanding outward from a focal point, which is related to the frustum) may define the relationship between foreground and background objects. If the geometric perspective is exaggerated, or if there are perspective cues such as lines receding to a vanishing point, the apparent depth of an image may be enhanced, which may make the image easier to view. While geometric perspective is not used in an exemplary embodiment of graphical system 100 (FIG. 1), in other embodiments geometric perspective may be used to complement the stereopsis scaling because it also enhances the stereopsis. For example, the frustum may be used to scale objects based on their distance z from viewer 122 (FIG. 1).

A lighting monoscopic depth cue may be based on the experience of viewer 122 (FIG. 1) that bright objects or objects with bright colors appear to be nearer than dim or darkly colored objects. In addition, the relative positions of proximate objects may be perceived by viewer 122 (FIG. 1) based on how light goes through the presented scene (e.g., solid objects versus non-solid objects). This monoscopic depth cue may be implemented by defining the position of a light source, defining transfer functions of the objects, and using the frustum. A similar monoscopic depth cue is depth cueing, in which the intensity of an object is proportional to the distance from viewer 122 in FIG. 1 (which may also be implemented using the frustum).

Shading may provide a related monoscopic depth cue because shadows cast by an object can make the object appear to be resting on a surface. Note that both lighting and shading may be dependent on a priori knowledge of viewer 122 (FIG. 1) because they involve viewer 122 (FIG. 1) understanding the light-source position (or the direction of the light) and how shadows in the scene will vary based on the light-source position.

Occlusion (or interposition) may provide a monoscopic depth cue based on the experience of viewer 122 (FIG. 1) that objects that are in front of others will occlude the objects that are behind them. Once again, this effect may be dependent on a priori knowledge of viewer 122 (FIG. 1). Note that lighting, shading and occlusion may also define and interact with motion parallax based on how objects are positioned relative to one another as viewer 122 (FIG. 1) moves relative to display 114 (FIG. 1). For example, the focal point of the light illuminating the object in a scene may change with motion and this change may be reflected in the lighting and the shading (similar to what occurs when an individual is moving in sunlight). Furthermore, the occlusion may be varied in a manner that is consistent with motion of viewer 122 (FIG. 1).

As described previously, the transfer functions that may be used to implement occlusion may be defined in graphical system 100 (FIG. 1) prior to graphics engine 112 in FIG. 1 (for example, by data engine 110 in FIG. 1). The transfer functions for objects may be used to modify the greyscale intensity of a given object after the projection on to the 2D viewing plane. In particular, during the projection on to the 2D viewing plane the average, maximum or minimum greyscale intensity projected into a given voxel may be used, and then may be modified by one or more transfer functions. For example, three sequential voxels in depth may have intensities of 50 to 100, −50 to 50, and −1000 to −50. These intensities may be modified according to a transfer function in which: greyscale values between 50 and 100 may have 0% intensity; greyscale values between −50 to 50 may have 100% intensity; and greyscale values between −1000 to −50 may have 50% intensity. In this way, the perspective may emphasize the second voxel and, to a lesser extent, the third voxel. In another example, transfer functions may be used to illustrate blood so that blood vessels appear filled up in the stereoscopic images, or to hide blood so that blood vessels appear open in the stereoscopic images.

Textural gradients for certain surfaces may also provide a monoscopic depth cue based on the experience of viewer 122 (FIG. 1) that the texture of a material in an object, like a grassy lawn or the tweed of a jacket, is more apparent when the object is closer. Therefore, variation in the perceived texture of a surface may allow viewer 122 (FIG. 1) to determine near versus far surfaces.

Computer System

Figure 6:
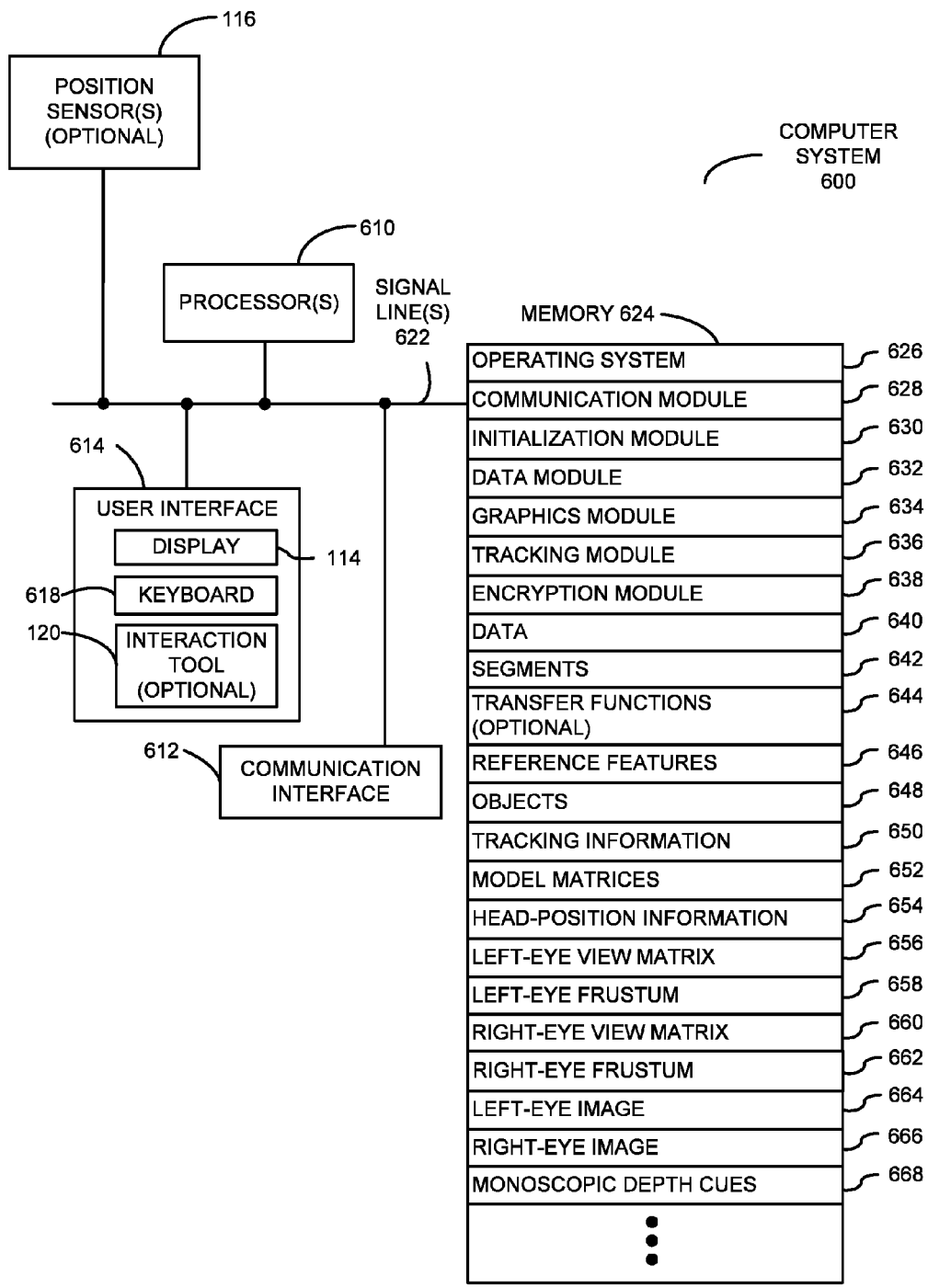
FIG. 6 is a block diagram illustrating a computer system in accordance with an embodiment of the present disclosure.

FIG. 6 presents a drawing of a computer system 600 that implements at least a portion of graphical system 100 (FIG. 1). This computer system includes one or more processing units or processors 610, a communication interface 612, a user interface 614, and one or more signal lines 622 coupling these components together. Note that the one or more processors 610 may support parallel processing and/or multi-threaded operation, the communication interface 612 may have a persistent communication connection, and the one or more signal lines 622 may constitute a communication bus. Moreover, the user interface 614 may include: a display 114, a keyboard 618, and/or an optional interaction tool 120 (such as a stylus, a pointer a mouse and/or a sensor or module that detects displacement of one or more of the user's fingers and/or hands).

Memory 624 in computer system 600 may include volatile memory and/or non-volatile memory. More specifically, memory 624 may include: ROM, RAM, EPROM, EEPROM, flash memory, one or more smart cards, one or more magnetic disc storage devices, and/or one or more optical storage devices. Memory 624 may store an operating system 626 that includes procedures (or a set of instructions) for handling various basic system services for performing hardware-dependent tasks. Memory 624 may also store procedures (or a set of instructions) in a communication module 628. These communication procedures may be used for communicating with one or more computers and/or servers, including computers and/or servers that are remotely located with respect to computer system 600.

Memory 624 may also include multiple program modules (or sets of instructions), including: initialization module 630 (or a set of instructions), data module 632 (or a set of instructions) corresponding to data engine 110 (FIG. 1), graphics module 634 (or a set of instructions) corresponding to graphics engine 112 (FIG. 1), tracking module 636 (or a set of instructions) corresponding to tool engine 118 (FIG. 1), and/or encryption module 638 (or a set of instructions). Note that one or more of these program modules (or sets of instructions) may constitute a computer-program mechanism. These program modules may be used to perform or implement: initialization, object identification and segmentation, virtual instruments, prehension and motion parallax, as well as the image processing rendering operations described previously.

Initialization

During operation, initialization module 630 may define parameters for image parallax and motion parallax. In particular, initialization module 630 may initialize a position of a camera in display 114 in a monoscopic view matrix by setting a position equal to the offset d between the viewing plane and the near plane of the frustum. (Alternatively, there may be a camera in optional interaction tool 120 that can be used to define the perspective. This may be useful in surgical planning.) For example, the offset d may be 1 ft or 0.3 m. Moreover, the focal point (0, 0, 0) may be defined as the center of the (x, y, z) plane and the +y axis may be defined as the 'up' direction.

Furthermore, the near and far planes in the frustum may be defined relative to the camera (for example, the near plane may be at 0.1 m and the far plane may be between 1.5-10 m), the right and left planes may be specified by the width in size 126 (FIG. 1) of display 114, and the top and bottom planes may be specified by the height in size 126 (FIG. 1) of display 114. Initialization module 630 may also define the interpupillary distance ipd equal to a value between 62 and 65 mm (in general, the ipd may vary between 55 and 72 mm). Additionally, initialization module 630 may define the display rotation angle θ (for example, θ may be 30°, where horizontal in 0°) and may initialize a system timer (sT) as well as tracking module 636 (which monitors the head position of viewer 122 in FIG. 1, the position of optional interaction tool 120, and which may monitor the gaze direction of viewer 122 in FIG. 1).

Then, initialization module 630 may perform prehension initialization. In particular, start and end points of optional interaction tool 120 may be defined. The start point may be at (0, 0, 0) and the end point may be at (0, 0, tool length), where tool length may be 15 cm.

Next, the current (prehension) position of optional interaction tool 120 (PresPh) may be defined, with a corresponding model matrix defined as an identity matrix. Moreover, a past (prehension) position of optional interaction tool 120 (PastPh) may be defined with a corresponding model matrix defined as an identity matrix. Note that prehension history of position and orientation of optional interaction tool 120 can be used to provide a video of optional interaction tool 120 movements, which may be useful in surgical planning.

In addition, initialization module 630 may initialize monoscopic depth cues. In some embodiments, a plane 25-30% larger than the area of display 114 is used to avoid edge effects and to facilitate the stereopsis scaling described previously. In some embodiments, the stereopsis scaling is adapted for a particular viewer based on factors such as: age, the wavelength of light in display 114, sex, the display intensity, etc. Moreover, the monoscopic depth-cue perspective may be set to the horizontal plane (0, 0, 0), and the monoscopic depth-cue lighting may be defined at the same position and direction as the camera in the view matrix.

Object Identification and Segmentation

Figure 7:
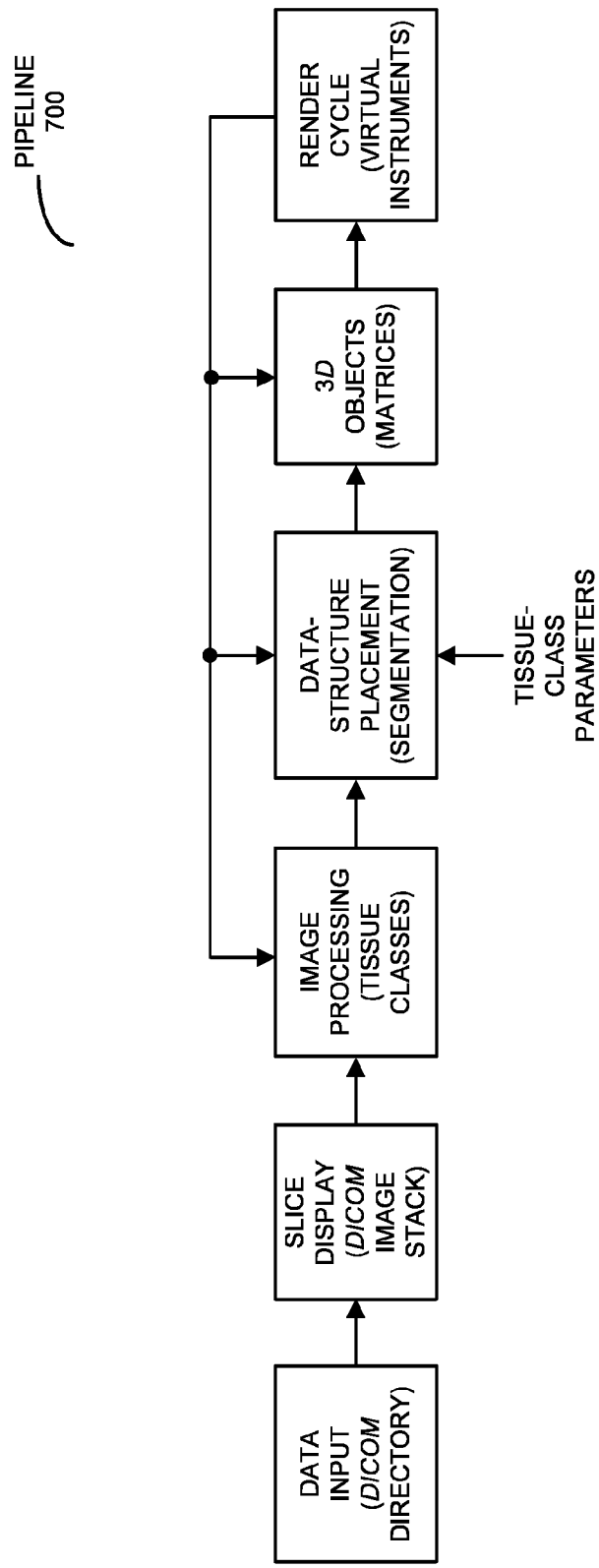
FIG. 7 is a block diagram illustrating a pipeline performed by the computer system of FIG. 6 in accordance with an embodiment of the present disclosure.

After the initialization is complete, data module 632 and graphics module 634 may define or may receive information from the user specifying: segments 642, optional transfer functions 644, reference features 646 and objects 648 in data 640. These operations are illustrated in FIG. 7, which presents a drawing illustrating a pipeline 700 performed by computer system 600 in FIG. 6. In particular, data 640 in FIG. 6 may include a DICOM directory with multiple DICOM images (i.e., source image data from one or more imaging devices), such as a series of 2D images that together depict a volumetric space that contains the anatomy of interest. Data module 632 in FIG. 6 may parse DICOM labels or tags associated with the DICOM images so that a number of images in the series are extracted along with their associated origin coordinate, orientation and voxel x,y and z spacing. (Note that, in general, data 640 may be isometric or non-isometric, i.e., dx, dy and dz may be the same or may be different from each other.) Then, each image of the series is loaded according to its series number and compiled as a single 3D collection of voxels, which includes one or more 3D objects 648 in FIG. 6 (and is sometimes referred to as a 'DICOM image object' or a 'clinical object').

Next, data module 632 may dimensionally scale (as opposed to the stereopsis scaling) the DICOM image object. For example, data module 632 may scale all the x voxels by multiplying their spacing value by 0.001 to assure the dimensions are in millimeters. Similarly, data module 632 may scale all the y voxels and all the z voxels, respectively, by multiplying their spacing values by 0.001 to assure the dimensions are in millimeters. This dimensional scaling may ensure that the voxels have the correct dimensions for tracking and display.

Furthermore, data module 632 may map the DICOM image object on to a plane with its scaled dimensions (i.e., the number of x voxels and the number of y voxels) and may be assigned a model matrix with its original orientation and origin. In some embodiments, graphics engine 634 in FIG. 6 optionally displays a stack of images (which is sometimes referred to as a 'DICOM image stack') corresponding to the DICOM image object in the plane.

Subsequently, via iterative interaction with graphics engine 634 and/or the user, data module 632 may aggregate or define several object lists that are stored in reference features 646 in FIG. 6. These object lists may include arrays of objects 648 that specify a scene, virtual instruments (or 'virtual instrument objects), or clinical objects (such as the DICOM image object), and may be used by graphics engine 634 to generate and render stereoscopic images (as described previously). A 'scene' includes 3D objects that delimit the visible open 3D space. For example, a scene may include a horizontal plane that defines the surface work plane on which all 3D objects in the DICOM image object are placed. Moreover, 'virtual instruments' may be a collection of 3D objects that define a specific way of interacting with any clinical target, clinical anatomy or clinical field. In particular, a virtual instrument includes: a 'representation' that is the basic 3D object elements (e.g., points, lines, planes) including a control variable; and an 'instrument' that implements the interaction operations based on its control variables to its assigned clinical target, clinical anatomy or clinical field. Note that a 'clinical field' may be a clinical object that defines a region within the DICOM image object that contains the anatomy of interest; 'clinical anatomy' may be a clinical object that defines the organ or tissue that is to be evaluated; and a 'clinical target' may be a clinical object that defines the region of interest of anatomy that is the candidate to be diagnosed or evaluated. (Clinical fields, clinical anatomy and clinical targets may be determined by the user and/or data module 632 during a segmentation process, which is described further below.) Note that, in some embodiments, a virtual instrument includes a software-extension of optional interaction tool 120 which can perform specific interaction tasks or operations. Furthermore, note that the user: cannot interact with scenes; may only be able to interact with virtual instruments through their control variables; and may have free interaction with clinical objects.

During iterative interaction, data module 632 may perform image processing on the DICOM image object to identify different levels of organ or tissue of interest. In particular, for the clinical field, the DICOM image object may be processed to identify different tissue classes (such as organ segments, vessels, etc.) as binary 3D collections of voxels based on the voxel values, as well as the boundaries between them. In the discussion that follows, a probability-mapping technique is used to identify the tissue classes. However, in other embodiments, different techniques may be used, such as: a watershed technique, a region-growing-from-seeds technique, or a level-set technique.

In the probability-mapping technique, a probability map (P) is generated using a 3D image with the same size as one of the DICOM images. The values of P may be the (estimated) probability of voxels being inside, outside and at the edge of the organ of interest. For each voxel, P may be obtained by computing three (or more) probabilities of belonging to tissue classes of interest, such as: voxels inside the organ (tissue class w1), voxels outside the organ (tissue class w2), and voxels at the interface between organs (tissue class w3). For a given voxel, P may be determined from the maximum of these three probabilities. Note that each probability may be calculated using a cumulative distribution function, e.g., $$F(x, x_o, \gamma) = \frac{1}{\pi} \cdot \arctan\left(\frac{x - x_o}{\gamma}\right) + \frac{1}{2},$$

where $x_o$ is the density of the tissue class, x is the density of the tested voxel, and y is a scale parameter of the distribution or the half-width at half-maximum.

The voxels at the interface between the tissue classes may be calculated for a neighborhood of voxels as being part of tissue class w1 or tissue class w2, and then averaging the result. Pseudo-code for this calculation for an omni-directional configuration with 27 neighboring voxels is shown in Table 1.

TABLE 1

```
for each voxel (x, y, z) do
    sum=0;
    for i = -1 to 1 do
        for j = -1 to 1 do
            for k = -1 to 1 do
                sum += P(w1j(x + i, y + j, z + k));
                sum += P(w2j(x + i, y + j, z + k));
            end;
        end;
    end;
    P(w3j(x, y, z)) = sum/27;
end
```

Additionally, during the iterative interaction data module 632 may perform image processing on the DICOM image object to identify the clinical anatomy. In particular, using the organ binary mask a ray-casting technique can be applied to generate a volume image of the organ of interest, such as the liver or another solid organ. Furthermore, using the boundary-voxel mask, a surface can be generated of the tissue using a marching-cube technique, such as the surface of a vessel (e.g., the large intestine or an artery). Note that other surfaces or ray-casting volumes can be generated from the segmented data.

In an exemplary embodiment, the determined clinical field may be the chest, the clinical anatomy may be the aorta, and the clinical target may be the aortic valve. Alternatively, the clinical field may be the abdomen, the clinical anatomy may be the colon, and the clinical target may be the one or more polyps.

After the image processing, data module 632 may perform the segmentation process (including data-structure processing and linking) to identify landmarks and region-of-interest parameters. The objective of the segmentation process is to identify functional regions of the clinical anatomy to be evaluated. This may be accomplished by an articulated model, which includes piecewise rigid parts for the anatomical segments coupled by joints, to represent the clinical anatomy. The resulting segments 642 in FIG. 6 may each include: a proximal point (S) location specified by the DICOM image-voxel index coordinate ($i_1, j_1, k_1$); a distal point (D) location specified by the DICOM image-voxel index coordinate ($i_2, j_2, k_2$); a central point (C) location specified by the DICOM image-voxel index coordinate ($i_3, j_3, k_3$), which may be the half point of the Euclidean distance between S and D; image-voxel index bounds (B) of the region of interest surrounding the central point including the proximal and distal points ($i_{min}, i_{max}, j_{min}, j_{max}, k_{min}, k_{max}$); and the corresponding world x, y, z coordinates of the central point and the region bounds locations calculated by accounting for the x, y, z voxel spacing of the source DICOM image. In general, segments 642 may be determined using an interactive segmentation technique with the user and/or a computer-implemented segmentation technique.

In the interactive segmentation technique, the user may select or specify n voxel index locations from the clinical field, which may be used to define the central points (Cs). Then, a 3D Voronoi map (and, more generally, a Euclidean-distance map) may determine regions around each of the selected index locations. For each of the Voronoi regions and each of the n voxel indexes, data module 632 may obtain: the minimum voxel index along the x axis of the DICOM image ($i_{min}$); the maximum voxel index along the x axis of the DICOM image ($i_{max}$); the minimum voxel index along the y axis of the DICOM image ($j_{min}$); the maximum voxel index along the y axis of the DICOM image ($j_{max}$); the minimum voxel index along the z axis of the DICOM image ($k_{min}$); and the maximum voxel index along the z axis of the DICOM image ($k_{max}$). Next, data module 632 may define: the proximal S point as $i_{min}, j_{min}, k_{min}$; and the distal D point as $i_{max}, j_{max}, k_{max}$. Moreover, data module 632 may generate a list of 3D objects (such as anatomical segments) of the clinical anatomy based on these values and may add these 3D objects to the object list of clinical objects in reference features 646 for use by graphics module 634.

Figure 8:
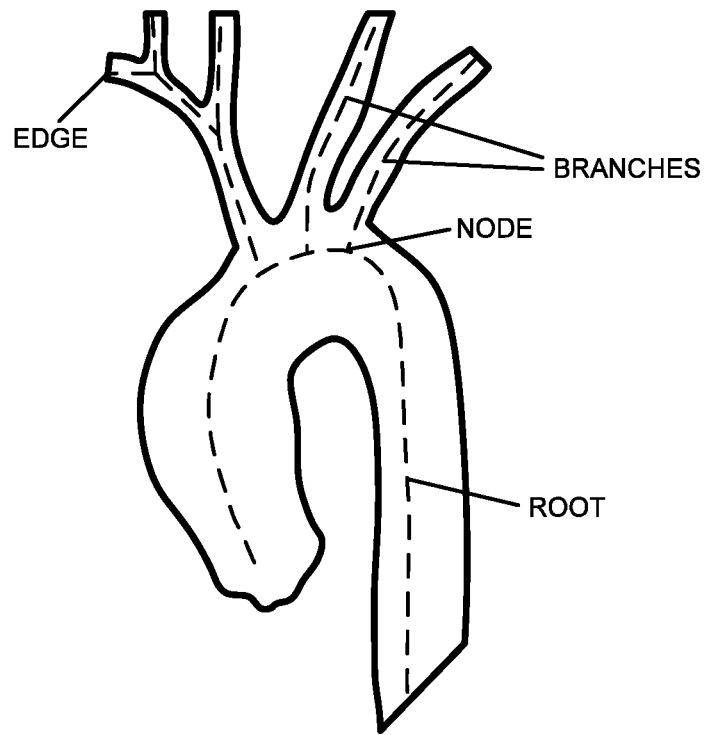
FIG. 8 is a drawing illustrating target segmentation in accordance with an embodiment of the present disclosure.
Figure 8:
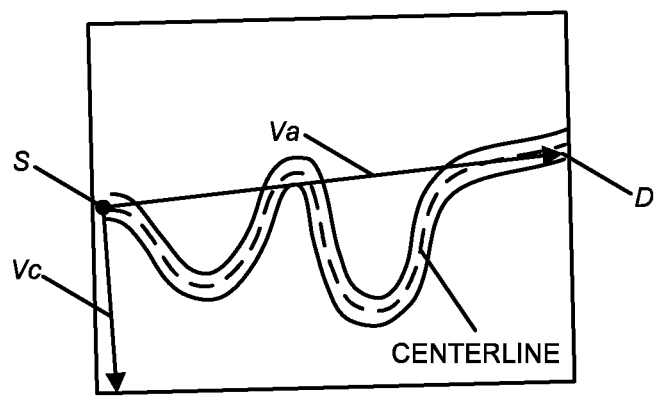

The computer-implemented segmentation technique is illustrated in FIG. 8. Initially, a centerline may be calculated across the clinical field or the clinical anatomy of interest resulting in a rooted-tree or graph (with a hierarchical arrangement of nodes and branches) centerline structure, each of which represents anatomical segment (which may be delimited by two edges). Note that each of the anatomical segments is enclosed by a bounding box, which is aligned with the vector connecting the proximal S and the distal D points of the centerline.

For each of the anatomical segments, data module 632 may determine three vectors: vector A (Va) based on (D-S), vector B (Vb, not shown) based on the cross product of the vector along (0, 1, 0) with Va, and vector C (Vc) based on the cross product of Va with Vb.

Figure 9:
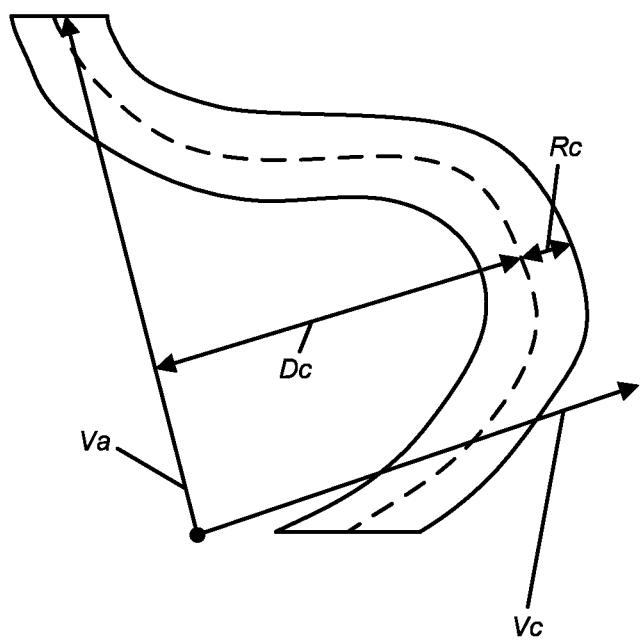
FIG. 9 is a drawing illustrating target segmentation in accordance with an embodiment of the present disclosure.

As shown in FIG. 9, presents a drawing illustrating segmentation, then each anatomical segment may be evaluated as a sampled centerline, where each sample point of the centerline is associated with a radius b (Rb, not shown) and a radius c (Rc) along the corresponding vectors Vb and Vc. Each of these radii is equal to the distance from the centerline sample point to the edge of the segmented anatomy.

Next, the dimensions of the bounding box may be calculated. The height may be the Euclidean length of Va plus the radii (Rb, Rc) associated with the two endpoints. The width may be twice the sum of the distance of the centerline point farthest from Va along Vb (Db, not shown) plus the radius Rb. And the depth may be twice the sum of the distance of the centerline point farthest from the Va along Vc (Dc) plus the radius Rc.

In FIG. 8, note that Vb (not shown) is perpendicular to Va and Vc and points out of the plane of the figure. Moreover, in FIG. 9, Rb (not shown) is perpendicular to Va and Vc and points out of the plane of the figure.

Figure 10:
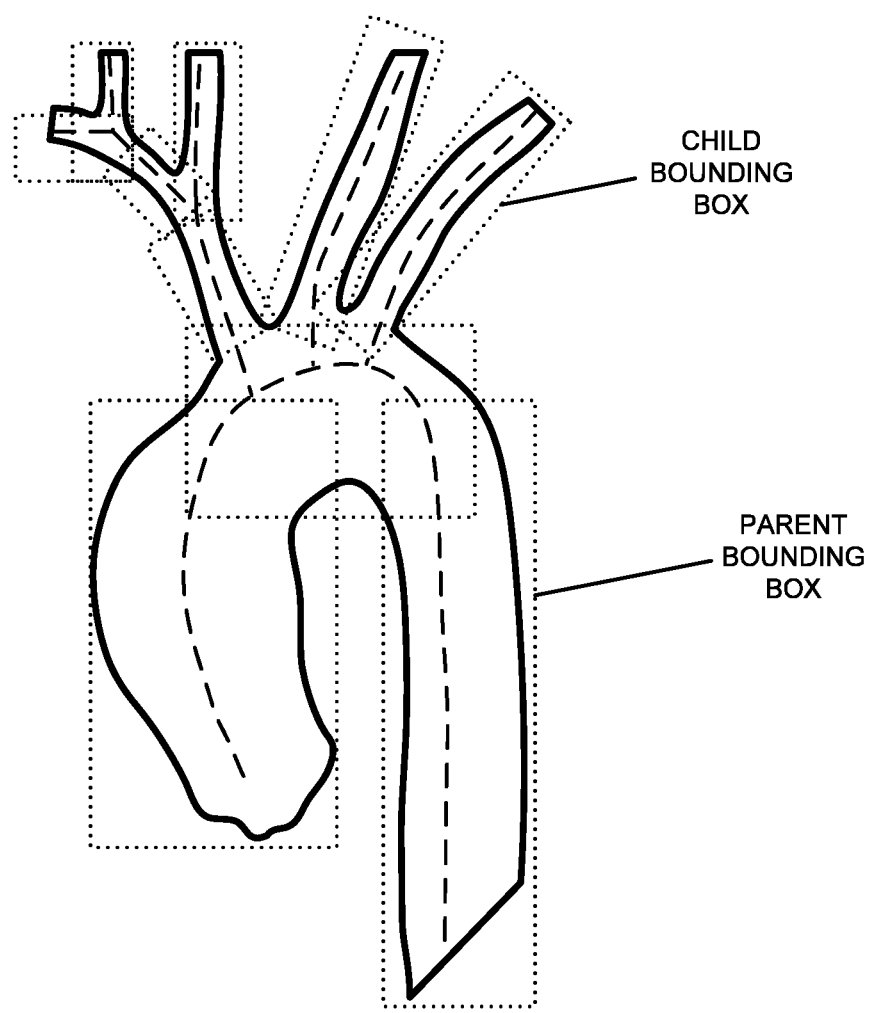
FIG. 10 is a drawing illustrating target segmentation in accordance with an embodiment of the present disclosure.

A natural kinematic constraint that the proximal point of a child anatomical segment must coincide with the distal point of the parent may be assumed for each parent-child pair. With this constraint, the configuration of the anatomical segments may be fully described by the individual anatomical-segment parts. As shown in FIG. 10, which illustrates the anatomical segments and their associated bounding boxes for the aorta, the resulting topology of the anatomical segments may be a rooted tree that is identical to the topology of the anatomical field, where the anatomical segments correspond to nodes and the kinematic constraints on the joints correspond to edges added to the anatomical field.

Figure 11:
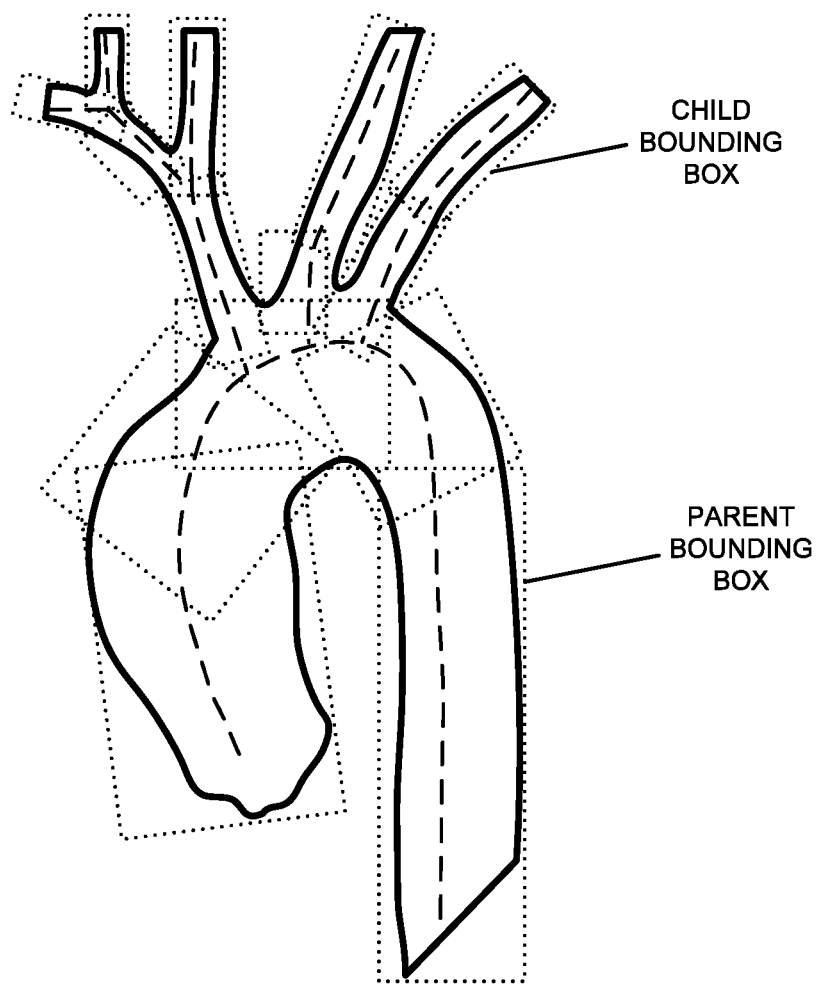
FIG. 11 is a drawing illustrating target segmentation in accordance with an embodiment of the present disclosure.

In order to approximate the geometry of an anatomical segment, the shape of bounding boxes may be kept thin. In particular, if the aspect ratio (width·depth)/height of the bounding box corresponding to an anatomical segment is greater than a threshold (such as 0.25 or 0.3), the segment may be subdivided into two nodes and an edge. Then, new bounding boxes may be computed for the two subdivided anatomical segments. In this way, the tree-structured articulated model may be iteratively constructed in a data-dependent manner. FIG. 11 shows the resulting anatomical segments and associated sub-divided bounding boxes. As summarized in Table 2, this tree-structured articulated model has root anatomical segments, with daughter or child branches with one or more anatomical segments. Extensible mark-up language pseudo-code for a data structure corresponding to a tree-structured articulated model is shown in Table 3.

TABLE 2

Root anatomical segment
    Anatomical segment 1
    Anatomical segment 2
    Branch 1
        Anatomical segment 1
        Anatomical segment 2
    Anatomical segment 3
    Branch 2
        Anatomical segment 1
        Anatomical segment 2
    Branch 3
        Anatomical segment 1
        Branch 4
            Anatomical segment 1
        Branch 5
            Anatomical segment 1
            Branch 6
                Anatomical segment 1
            Branch 7
                Anatomical segment 1
    Anatomical segment 4

TABLE 3

```xml
<?xml version="1.0" encoding="UTF-8"?>
<Anatomy id="Aorta">
  <root>
    <segment><!-- 1 -->
      <s>root-s1</s>
      <d>root-d1</d>
```

TABLE 3-continued

```xml
      <bounds>
        <imin>imin</imin>
        <imax>imax</imax>
        <jmin>jmin</jmin>
        <jmax>jmax</jmax>
        <kmin>kmin</kmin>
        <kmax>kmax</kmax>
      </bounds>
      <center>root-c1</center>
    </segment>
    <segment><!-- 2 -->
      <s>root-s2</s>
      <d>root-d2</d>
      <bounds>
        <imin>imin</imin>
        <imax>imax</imax>
        <jmin>jmin</jmin>
        <jmax>jmax</jmax>
        <kmin>kmin</kmin>
        <kmax>kmax</kmax>
      </bounds>
      <center>root-c2</center>
      <branch><!-- Branch 1 / 2 segments -->
        <segment>
          <s>branch1-s1</s>
          <d>branch1-d1</d>
          <bounds>
            <imin>imin</imin>
            <imax>imax</imax>
            <jmin>jmin</jmin>
            <jmax>jmax</jmax>
            <kmin>kmin</kmin>
            <kmax>kmax</kmax>
          </bounds>
          <center>branch1-c1</center>
        </segment>
  etc.
```

Once the segmentation is completed, a list of 3D objects (the anatomical segments) of the clinical anatomy defined by the data structures is generated and added to the list of clinical objects in reference features 646 for use by graphics module 634.

In an exemplary embodiment, using the interactive or the computer-based segmentation technique, the surface of the colon may be a single object or may be sub-divided into six segments or more. Depending on the tortuosity of the colon, this calculation may involve up to 13 iterations in order to obtain segments with the desired aspect ratios. Alternatively, an artery or a vein may be rendered as one or more objects that represents multiple subsets of a volume.

As described further below with reference to FIG. 17, the articulated model may facilitate: fast extraction of regions of interest, reduced storage requirements (because anatomical features may be described using a subset of the DICOM images or annotations within the DICOM images), faster generating and rendering of True 3D stereoscopic images with motion parallax and/or prehension, and a lower cost for the graphical system.

Virtual Instruments

As described previously in the discussion of image processing and rendering operations, graphics module 634 may generate 3D stereoscopic images. Furthermore, prior to rendering these 3D stereoscopic images and providing them to display 114, stereopsis scaling may be performed to enhance or optimize the stereo acuity of the user based on the maximum and minimum scale factors (i.e., the range of scaling) that can be applied to the anatomical segments dzmin and $dz_{max}$. During the rendering, once the anatomy has been adequately segmented and linked, graphics module 634 may also implement interaction using one or more virtual instruments. For example, a virtual instrument may allow the user to navigate the body parts, and to focus on and to evaluate a segment of a patient's anatomy, allowing the user to optimize workflow.

Each virtual instrument includes: a 'representation' which is the basic object elements (points, lines, planes, other 3D objects, etc.) including a control variable; and an 'instrument' which implements the interaction operations based on its control variables to its assigned clinical target, clinical anatomy or clinical field. While a wide variety of virtual instruments can be defined (such as a pointer or a wedge), in the discussion that follows a dissection cut plane, a bookmark to a region of interest, a problem-solving tool that combines a 3D view with a 2D cross-section, and an 'intuitive 2D' approach that allows the viewer to scroll through an array of 2D images using stylusare used as illustrative examples.

For the cut-plane virtual instrument, the representation includes: an origin point (Origin) that defines an origin $x_o$, $y_o$, $z_o$ position of the cut plane; point 1 that, in conjunction with the origin point, defines axis 1 ($a_1$) of the cut plane; and point 2 that, in conjunction with the origin point, defines axis 2 ($a_2$) of the cut plane. The normal to the cut plane points in the direction of the cross product of $a_1$ and $a_2$. Moreover, the center point (Center Point) is the control point of the cut plane. In particular, Center[$x$]=Origin[$x_o$]+0.5($a_1[x]+a_2[x]$), Center[$y$]=Origin[$y_o$]+0.5($a_1[y]+a_2[y]$), and Center[$z$]=Origin[$z_o$]+0.5($a_1[z]+a_2[z]$).

The user can control the cut plane by interacting with the center point, and can translate and rotate the cut plane using optional interaction tool 120 in FIG. 6. For example, the user can control a cut plane to uncover underlying anatomical features, thereby allowing the rest of the anatomical segment to be brought into view by rotating the anatomical segment. Note that the cut plane may modify the bounding-box coordinates of the anatomical segment by identifying the intersection points of the cut plane to the bounding box in the direction of the normal of the cut plane.

For the bookmark virtual instrument, the representation includes: point 1 that defines $x_{min}$, $y_{min}$ and $z_{min}$; point 2 that defines $x_{max}$, $y_{max}$ and $Z_{max}$. The bookmark may be specified by the center point and the bounds of the box ($x_{min}$, $x_{max}$, $y_{min}$, $y_{max}$, $z_{min}$, $z_{max}$). Moreover, the center point (Center Point) is the control point of the region of interest. In particular, Center[$x$]=0.5($x_{max}-x_{min}$), Center[$y$]=0.5($y_{max}-y_{min}$), and Center[$z$]=0.5($z_{max}-z_{min}$).

The user can control the bookmark by placing it at a center point of any clinical object with a box size equal to 1, or by placing a second point to define a volumetric region of interest. When the volumetric region of interest is placed, that region can be copied for further analysis. Note that using a bookmark, the user can specify a clinical target that can be added to the object list of clinical object for use by graphics module 634.

For the problem-solving virtual instrument, the representation combines a bookmark to a 3D region of interest and a cut plane for the associated 2D projection or cross-section. This representation is summarized in Table 4.

TABLE 4

| 2D Cross-Section | 3D Region of Interest |
|---|---|
| The origin point defines the position of a cut plane ($x_o$, $y_o$, $z_o$). Point 1 defines axis 1 ($a_1$) of the cut plane. Point 2 defines axis 2 ($a_2$) of the cut plane. The normal to the cut plane points in the direction of the cross product of $a_1$ with $a_2$. The center point is the control point of the cut plane. | Point 1 defines $x_{min}$, $y_{min}$ and $z_{min}$. Point 2 defines $x_{max}$, $y_{max}$ and $z_{max}$. The bookmark is defined by the center point and the bounds of the box ($x_{min}$, $x_{max}$, $y_{min}$, $y_{max}$, $z_{min}$, $z_{max}$). The center point is the control point. |

The user can control the problem-solving virtual instrument to recall a bookmarked clinical target or a selected region of interest of a 3D object and can interact with its center point. In this case, the surface of the 3D object may be transparent (as specified by one of optional transfer functions 644 in FIG. 6). The 2D cross-section is specified by a cut plane (defined by the origin, point 1 and point 2) that maps the corresponding 2D DICOM image of the cut plane within the region of interest. By interacting with the 2D cross-section center point, the user can determine the optimal 2D cross section image of a particular clinical target. Note that the problem-solving virtual instrument allows the user to dynamically interact with the 3D stereoscopic image and at least one 2D projection. As the user interacts with objects in these images, the displayed images may be dynamically updated. Furthermore, instead of merely rotating an object, the user may be able to 'look around' (i.e., motion parallax in which the object rotates in the opposite direction to the rotation of the user relative to the object), so that they can observe behind an object, and concurrently can observe the correct 2D projection.

Figure 12A:
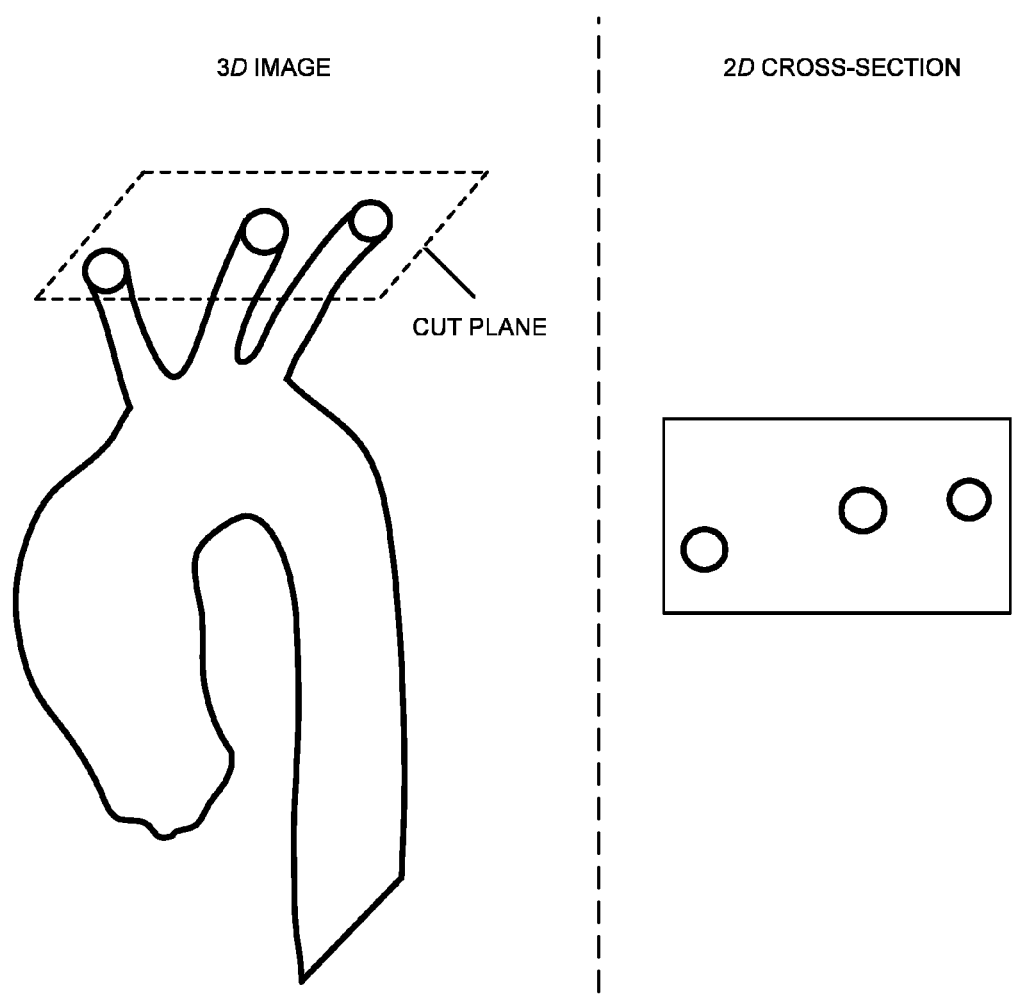
FIG. 12A is a drawing illustrating a display in the graphical system of FIG. 1 in accordance with an embodiment of the present disclosure.
Figure 12B:
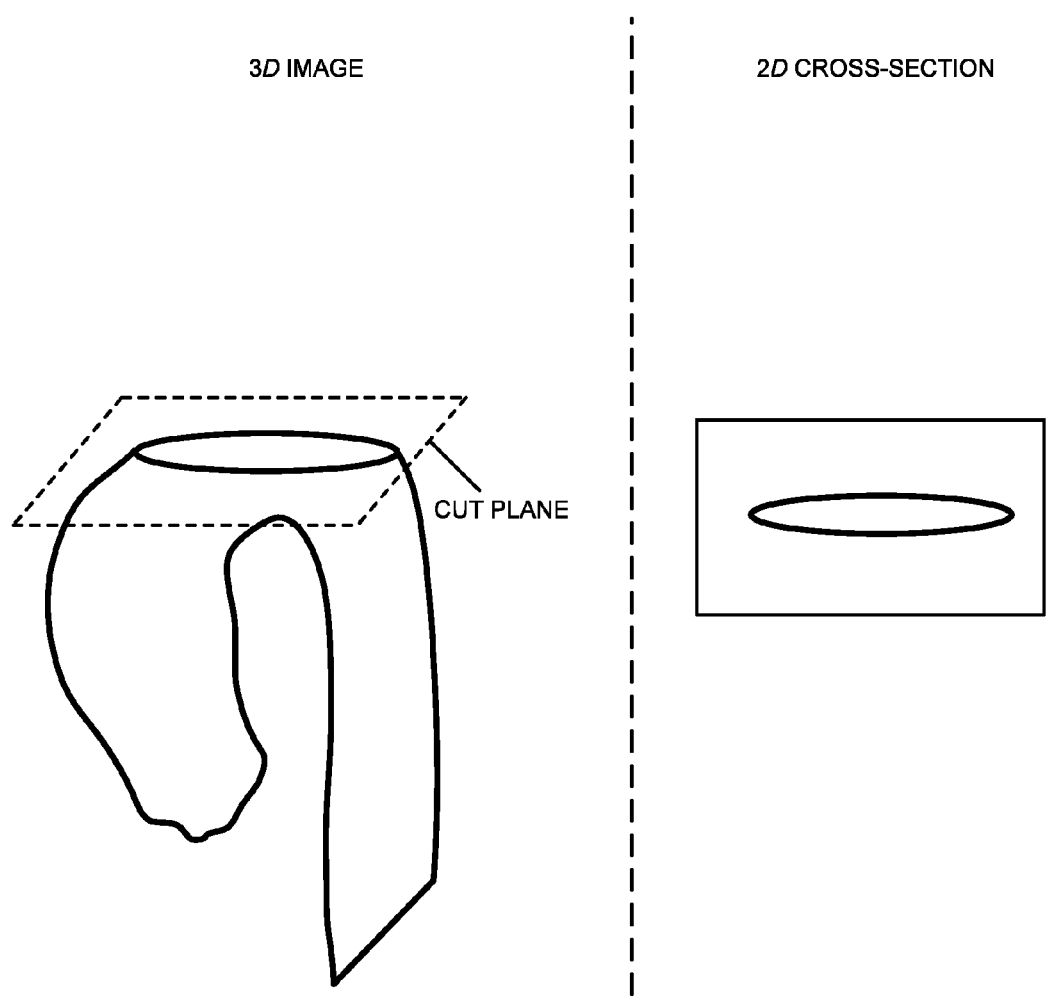
FIG. 12B is a drawing illustrating a display in the graphical system of FIG. 1 in accordance with an embodiment of the present disclosure.
Figure 12C:
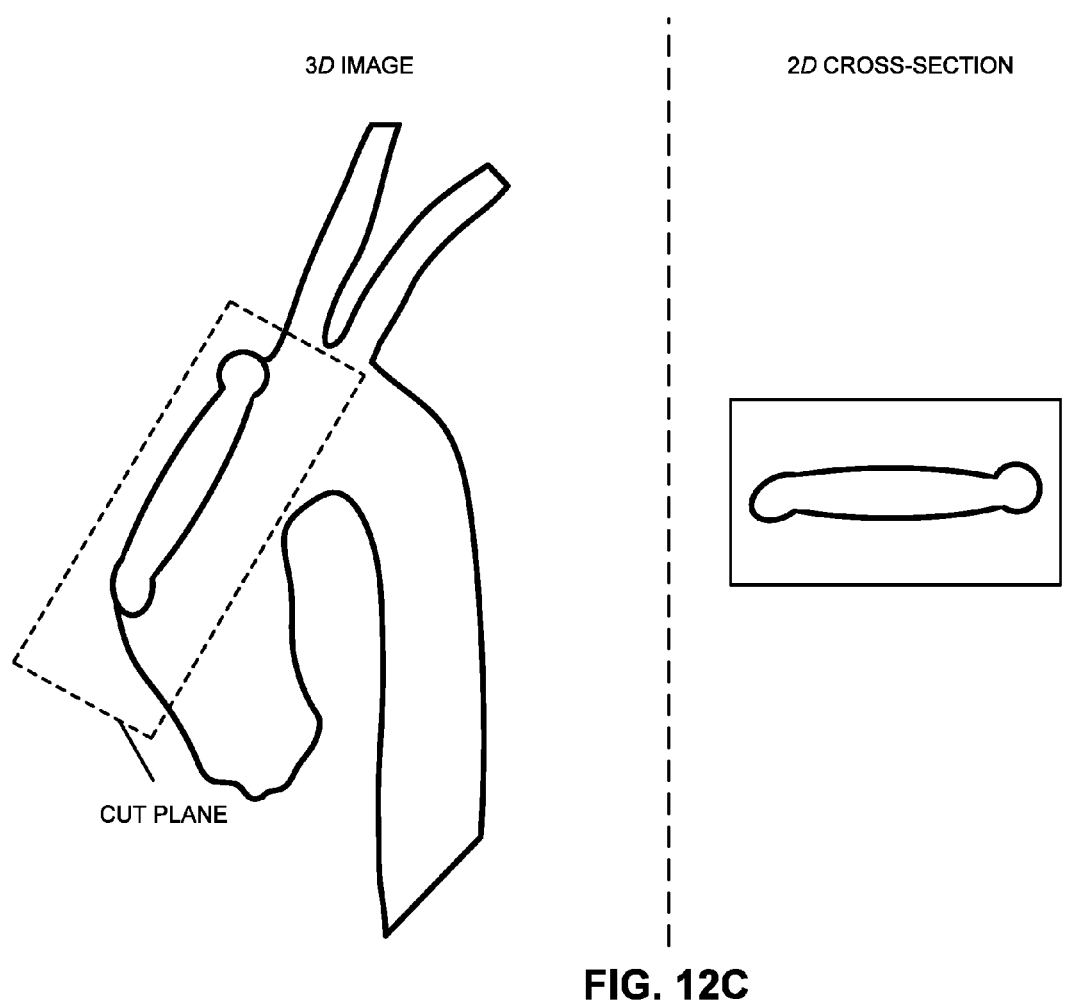
FIG. 12C is a drawing illustrating a display in the graphical system of FIG. 1 in accordance with an embodiment of the present disclosure.

This operation of the problem-solving virtual instrument is illustrated in FIGS. 12A-C, which shows the display of a 3D stereoscopic image and 2D projections side by side (such as on display 114 in FIGS. 1 and 6). When the user moves, changes their viewing direction or perspective and/or interacts with the object (in this case a rectangular cube) in the 3D stereoscopic image, graphics module 634 in FIG. 6 dynamically updates the 2D projection. This may allow the user to look around the object (as opposed to rotating it along a fixed axis). Moreover, by providing accurate and related 2D and 3D images, the problem-solving virtual instrument may allow a physician to leverage their existing training and approach for interpreting 2D images when simultaneously viewing 3D images. This capability is described further below with reference to FIG. 18.

The intuitive 2D virtual instrument presents a 2D image that is displayed as the viewer scrolls through an array of 2D images using a stylus (and, more generally, the optional interaction tool) or a scroll bar. This virtual instrument can improve intuitive understanding of the 2D images.

The intuitive 2D virtual instrument uses a 3D volumetric image or dataset that includes the 2D images. These 2D images include a collection of voxels that describe a volume, where each voxel has an associated 4×4 model matrix. Moreover, the representation for the intuitive 2D virtual instrument is a fixed cut plane, which specifies the presented 2D image (i.e., voxels in the dataset that are within the plane of interaction with the cut plane). The presented 2D image is at position (for example, an axial position) with a predefined center (x, y, z position) and bounds ($x_{min}$, $x_{max}$, $y_{min}$, $y_{max}$, $z_{min}$, $z_{max}$). The cut plane, which has a 4×4 rotation matrix with a scale of one, is a two-dimensional surface that is perpendicular to its rotation matrix. Note that the cut plane can be defined by: the origin of the cut plane (which is at the center of the presented 2D image), the normal to the current plane (which is the normal orientation of the presented 2D image), and/or the normal matrix N of the reference model matrix M for the presented 2D image (which defines the dimensions, scale and origin for all of the voxels in the presented 2D image), where N is defined as the transpose (inverse(M)). Another way to define the cut plane is by using the forward (pF) and backward point (pB) of the stylus or the optional interaction tool. By normalizing the interaction-tool vector, which is defined as $$\frac{pF - pB}{|pF - pB|},$$

normal of the cut plane is specified, and the forward point of the stylus of the optional interaction tool specifies the center of the cut plane.

In the intuitive 2D virtual instrument, the normal of the cut plane defines the view direction in which anything behind the cut plane can be seen by suitable manipulation or interaction with the cut plane, while anything in front of the cut plane cannot be seen. Because the dataset for the intuitive 2D virtual instrument only includes image data (e.g., texture values) only the voxel values on the cut plane are displayed. Therefore, transfer functions and segmentation are not used with the intuitive 2D virtual instrument.

By translating/rotating the cut plane using the stylus (or the scroll bar), the viewer can display different oblique 2D image planes (i.e., different 2D slices or cross-sections in the dataset). If the viewer twists their wrist, the intuitive 2D virtual instrument modifies the presented 2D image (in a perpendicular plane to the stylus direction). In addition, using the stylus the viewer can go through axial, saginal or coronal views in sequence. The viewer can point to a pixel on the cut plane and can push it forward to the front.

During interaction with the viewer, for the cut plane the intuitive 2D virtual instrument uses the stylus coordinates to perform the operations of: calculating a translation matrix (Tr) between the past and present position; calculating the rotation (Rm) between the past and present position; calculating the transformation matrix (Tm) equal to −Tr·Rm·Tr; and applying the transformation to the reference model matrix. Thus, the cut plane is only rotated, while translations forward or backward in the slides are canceled out. Similarly, for the presented 2D image, the intuitive 2D virtual instrument uses the stylus coordinates to perform the operations of: calculating a translation matrix (Tr) between the past and present position; calculating the rotation (Rm) between the past and present position; calculating the transformation matrix (Tm) equal to Rm·(−Tr); and applying the transformation to the reference model matrix. Thus, the presented 2D image includes translations (moving forward or backward in the slides) and includes a 2D slice at an arbitrary angle with respect to fixed (or predefined) 2D data slices based on manipulations in the plane of the cut plane.

Figure 13:
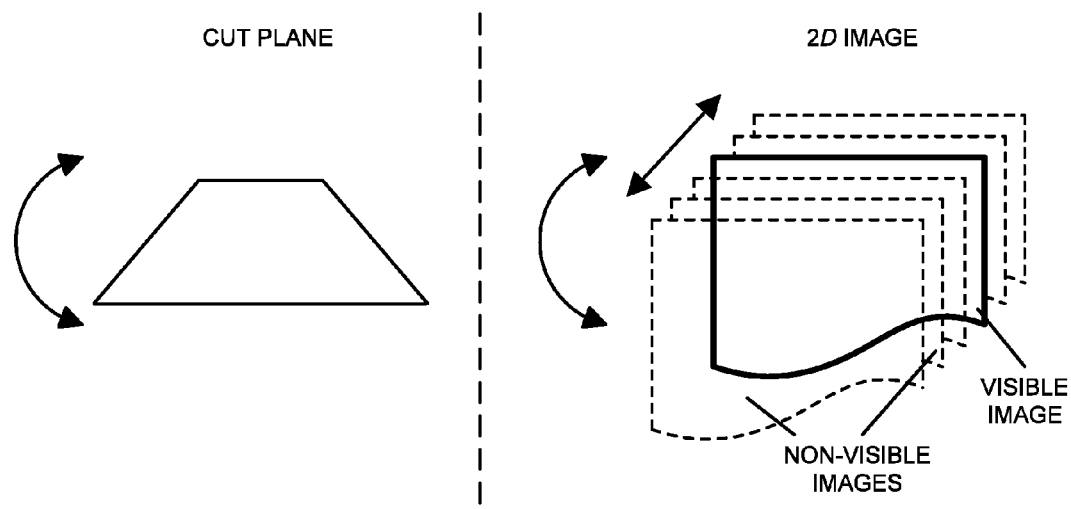
FIG. 13 is a drawing illustrating a virtual instrument in accordance with an embodiment of the present disclosure.

The interaction is illustrated in FIG. 13, which shows the cut plane and the presented 2D image side by side (such as on display 114 in FIGS. 1 and 6) for the intuitive 2D virtual instrument. (In addition, non-visible 2D images surrounding the presented 2D image are illustrated in FIG. 13 using dashed lines.) Based on manipulation of the stylus by the viewer (which can include rotations and/or translations), the cut plane is rotated, while the presented 2D image is translated and/or rotated to uncover voxels.

Prehension and Motion Parallax

Referring back to FIG. 6, tracking module 636 may track the position of optional interaction tool 120, for example, using one or more optional position sensors 116. The resulting tracking information 650 may be used to update the position of optional interaction tool 120 (e.g., PastPh equals PresPh, and PresPh equals the current position of optional interaction tool 120). Graphics module 634 may use the revised position of the optional interaction tool 120 to generate a revised transformation model matrix for optional interaction tool 120 in model matrices 652.

Next, tracking module 636 may test if optional interaction tool 120 is touching or interfacing with one of objects 648 shown in display 114 (note, however, that in some embodiments viewer 122 in FIG. 1 cannot interact with some of reference features 646 using optional interaction tool 120). If yes, the position and orientation of optional interaction tool 120 may be modified, with a commensurate impact on the transformation model matrix in model matrices 652 for optional interaction tool 120. In particular, the translation to be applied to the one of objects 648 (Delta Vector) may be determined based on the x, y and z position of the tool tip (ToolTip) (which is specified by PresPh) and the x, y and z position where optional interaction tool 120 touches the one of objects 648 (ContactPoint) using DeltaVector[x]=ToolTip[x]−ContactPoint[x], DeltaVector[y]=ToolTip[y]−ContactPoint[y], and DeltaVector[z]=ToolTip[z]−ContactPoint[z].

The rotation to be applied may be determined using a local variable (in the form of a 4×4 matrix) called ROT. Initially, ROT may be an identity matrix. The rotation elements of ROT may be determined by matrix multiplying the rotation elements specified by PresPh and the rotation elements specified by PastPh. Then, the following transformation operations are concatenated and applied to the model matrix of the one of objects 648 using a local 4×4 matrix T (which initially includes all 16 elements in the current model matrix: translate T to the negative of the center position of the one of objects 648 (−Center[x], −Center[y], −Center[z]) to eliminate interaction jitter; rotate T by ROT; translate T to the object center (Center[x], Center[y], Center[z]) to eliminate interaction jitter; and translate T to Delta Vector (DeltaVector[x], DeltaVector[y], DeltaVector[z]). Next, the model matrix is replaced with the T matrix.

Note that calculations related to the position of optional interaction tool 120 may occur every 15 ms or faster so that prehension related to optional interaction tool 120 is updated at least 66.67 times per second.

Moreover, tracking module 636 may track the head position of viewer 122 (FIG. 1), for example, using one or more optional position sensors 116. Updates to head-position information 654 may be applied by graphics module 634 to the virtual space and used to render left-eye and right-eye images for display on display 114. In particular, the inverse of left-eye view matrix 656 may be revised by: translating the object relative to the position coordinate of the camera (the monoscopic view matrix $V_O$ that is located at the center of display 114); rotating by θ−90° (which specifies a normal to an inclined display); and translating to the eye of the viewer 122 in FIG. 1 by taking away the original offset d, translating to the current head position and translating left to 0.5 ipd. Thus, $$V_{left\_eye}^{-1} = V_0^{-1} \cdot Rv(\theta - 90°) \cdot Tv(-d) \cdot Tv(\text{head\_position}) \cdot Tv\left(\frac{-ipd}{2}, 0, 0\right).$$

Similarly, left-eye frustum 658 may be revised by: translating to the current head position relative to the offset k (shown in FIGS. 3 and 4) between the eyes of viewer 122 in FIG. 1 and the viewing plane; and translating left to 0.5 ipd. Thus, $$F_{left\_eye} = Tv(0, 0, k) \cdot Tv(\text{head\_position}) \cdot Tv\left(\frac{-ipd}{2}, 0, 0\right).$$

These operations may be repeated for the right eye to calculate right-eye view matrix 660 and right-eye frustum 662, i.e., $$V_{right\_eye}^{-1} = V_0^{-1} \cdot Rv(\theta - 90°) \cdot Tv(-d) \cdot Tv(\text{head\_position}) \cdot Tv\left(\frac{-ipd}{2}, 0, 0\right).$$

and $$F_{right\_eye} = Tv(0, 0, k) \cdot Tv(\text{head\_position}) \cdot Tv\left(\frac{-ipd}{2}, 0, 0\right).$$

Using the left-eye and the right-eye view and frustum matrices 656-662, graphics module 634 may determine left-eye image 664 for a given transformation model matrix Mt in model matrices 652 based on $$Mt \cdot V_{left\_eye} \cdot F_{left\_eye},$$

and may determine right-eye image 666 for the given transformation model matrix Mt based on $$Mt \cdot V_{right\_eye} \cdot F_{right\_eye},$$

After applying monoscopic depth cues 668, graphics module 634 may display left-eye and right-eye images 666 and 668 on display 114. Note that calculations related to the head position may occur at least every 50-100 ms, and the rendered images may be displayed on display 114 at a frequency of at least 60 Hz for each eye.

In general, objects are presented in the rendered images on display 114 with image parallax. However, in an exemplary embodiment the object corresponding to optional interaction tool 120 on display 114 is not be represented with image parallax.

Therefore computer system 600 may implement a data-centric approach (as opposed to a model-centric approach) to generate left-eye and right-eye images 664 and 666 with enhanced (or optimal) depth acuity for discrete-sampling data. However, in other embodiments the imaging technique may be applied to continuous-valued or analog data. For example, data module 632 may interpolate between discrete samples in data 640. This interpolation (such as minimum bandwidth interpolation) may be used to resample data 640 and/or to generate continuous-valued data.

While the preceding discussion illustrated left-eye and right-eye frustums with near and far (clip) planes that can cause an object to drop out of left-eye and right-eye images 664 and 666 if viewer 122 (FIG. 1) moves far enough away from display 114, in some embodiments the left-eye and right-eye frustums provide a more graceful decay as viewer 122 (FIG. 1) moves away from display 114. Furthermore, when the resulting depth acuity in left-eye and right-eye images 664 and 666 is sub-optimal, intuitive clues (such as by changing the color of the rendered images or by displaying an icon in the rendered images) may be used to alert viewer 122 (FIG. 1).

Furthermore, while the preceding embodiments illustrated prehension in the context of motion of optional interaction tool 120, in other embodiments additional sensory feedback may be provided to viewer 122 (FIG. 1) based on motion of optional interaction tool 120. For example, haptic feedback may be provided based on annotation, metadata or CT scan Hounsfield units about materials having different densities (such as different types of tissue) that may be generated by data module 632. This haptic feedback may be useful during surgical planning or a simulated virtual surgical procedure.

Because information in computer system 600 may be sensitive in nature, in some embodiments at least some of the data stored in memory 624 and/or at least some of the data communicated using communication module 628 is encrypted using encryption module 638.

Instructions in the various modules in memory 624 may be implemented in: a high-level procedural language, an object-oriented programming language, and/or in an assembly or machine language. Note that the programming language may be compiled or interpreted, e.g., configurable or configured, to be executed by the one or more processors 610.

Although computer system 600 is illustrated as having a number of discrete components, FIG. 6 is intended to be a functional description of the various features that may be present in computer system 600 rather than a structural schematic of the embodiments described herein. In some embodiments, some or all of the functionality of computer system 600 may be implemented in one or more application-specific integrated circuits (ASICs) and/or one or more digital signal processors (DSPs).

Computer system 600, as well as electronic devices, computers and servers in graphical system 100 (FIG. 1), may include one of a variety of devices capable of performing operations on computer-readable data or communicating such data between two or more computing systems over a network, including: a desktop computer, a laptop computer, a tablet computer, a subnotebook/netbook, a supercomputer, a mainframe computer, a portable electronic device (such as a cellular telephone or PDA), a server, a portable computing device, a consumer-electronic device, a Picture Archiving and Communication System (PACS), and/or a client computer (in a client-server architecture). Moreover, communication interface 612 may communicate with other electronic devices via a network, such as: the Internet, World Wide Web (WWW), an intranet, a cellular-telephone network, LAN, WAN, MAN, or a combination of networks, or other technology enabling communication between computing systems.

Graphical system 100 (FIG. 1) and/or computer system 600 may include fewer components or additional components. Moreover, two or more components may be combined into a single component, and/or a position of one or more components may be changed. In some embodiments, the functionality of graphical system 100 (FIG. 1) and/or computer system 600 may be implemented more in hardware and less in software, or less in hardware and more in software, as is known in the art.

Applications

By combining image parallax, motion parallax, prehension and stereopsis scaling to create an interactive stereo display, it is possible for users of the graphical system to interact with displayed 3D objects as if they were real objects. For example, physicians can visually work with parts of the body in open 3D space. By incorporating the sensory cues associated with direct interaction with the displayed objects, it is believed that both cognitive and intuitive skills of the users will be improved. This is expected to provide a meaningful increase in the user's knowledge.

In the case of medicine, this cognitive-intuitive tie can provide a paradigm shift in the areas of diagnostics, surgical planning and a virtual surgical procedure by allowing physicians and medical professionals to focus their attention on solving clinical problems without the need to struggle through the interpretation of 3D anatomy using 2D views. This struggle, which is referred to as 'spatial cognition,' involves viewing 2D images and constructing a 3D recreation in your mind (a cognitively intensive process). In the absence of the True 3D provided by the graphical system, the risk is that clinically significant information may be lost. The True 3D provided by the graphical system may also address the different spatial cognitive abilities of the physicans and medical professionals when performing spatial cognition.

In the discussion that follows, virtual colonoscopy is used as an illustrative example of the application of the graphical system and True 3D. However, in other embodiments the graphical system and True 3D are used in a wide variety of applications, including medical applications (such as mammography) and non-medical applications.

In True 3D virtual colonoscopy (which is sometimes referred to as 'True 3D computed tomography colonography' or 'True 3D-CTC'), a reader (such as a physician) may: select a CTC case; process the CTC case images to extract a 3D model of the colon lumen and flag polyp candidates; and implement a True 3D-CTC interpretation process to locate and evaluate polyps. After selecting a CTC case, the reader can view the CT images and scroll through them in open 3D space using a hand-directed stylus as the optional interaction tool to assess their diagnostic quality while the images are processed in the background by the graphical system.

When processing the CTC case images, the graphical system may read in the DICOM directory and may optionally display the DICOM image stack, as described previously with reference to FIG. 7. Then, during the object identification and segmentation, the graphical system may segment the colon by obtaining a probability map P. In particular, for each voxel the graphical system may calculate three probabilities of belonging to each of the three tissue classes of interest (air, liquid and interface, where the union of these three tissue classes forms the inside of the colon), and then taking P as the maximum of these three probabilities. Because the greyscale distributions of air (tissue class w1) and liquid (tissue class w2) are usually very distinguishable and stable in different studies, they can be empirically learned by manually segmenting these two tissue classes in a given CT study, and then constructing the probability distribution functions $p(x_j, w1)$ and $p(xj, w2)$ by standard kernel-density estimation.

Figure 14:
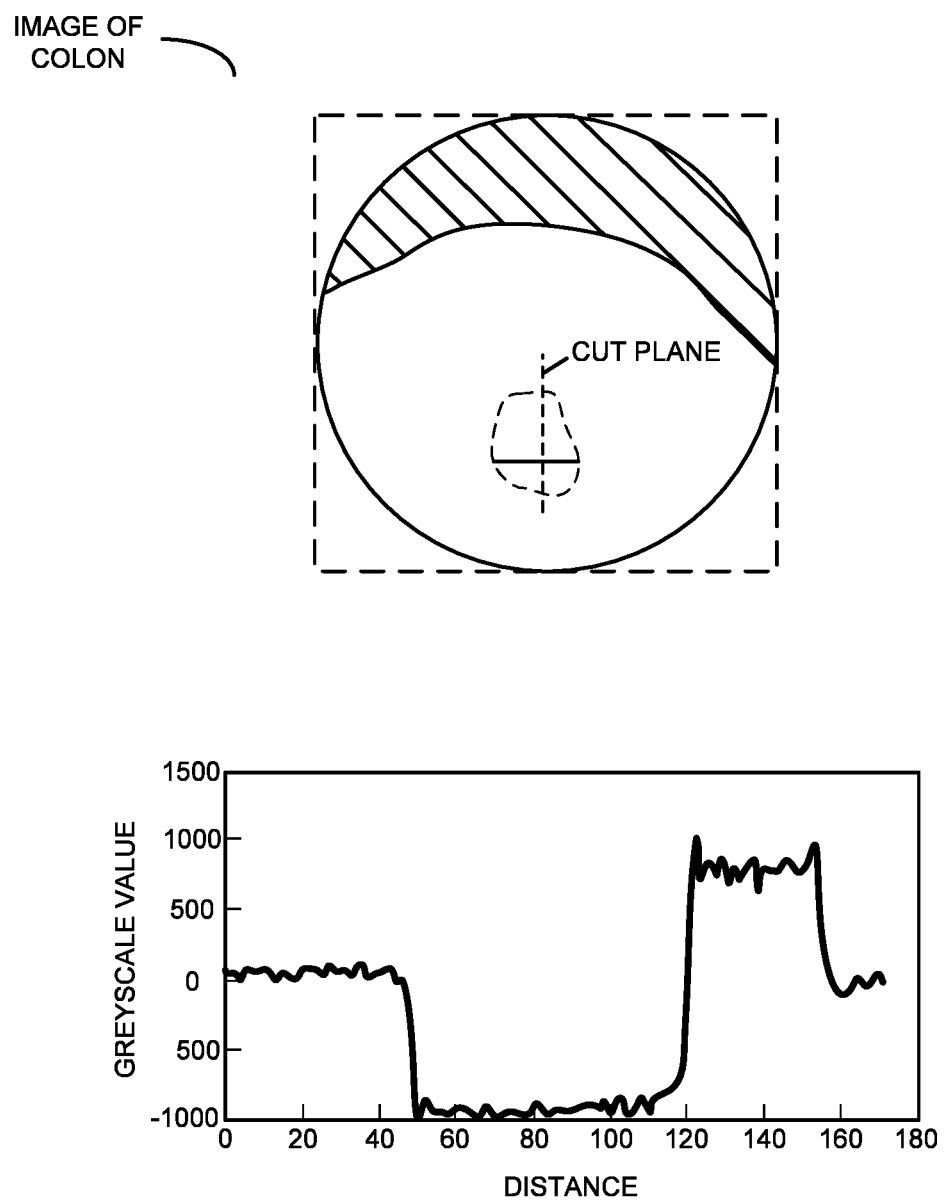
FIG. 14 is a drawing illustrating segmentation in virtual colonoscopy in accordance with an embodiment of the present disclosure.

This is illustrated in FIG. 14, which presents segmentation in virtual colonoscopy (including defining values of $x_o$ and $\gamma$ for different tissue classes or pixel types along a cut plane through the colon). In this figure, the chart depicts the 1D values of the cut plane going across the abdomen soft tissue, from the air-filled colon lumen to the contrast-filled colon lumen. Thus, the 1D values start around +50 (or close to zero) for soft tissue, drop down to near −1000 for air, rise sharply up to the contrast near +1000, and then back to the soft tissue. Therefore, in an exemplary embodiment, the tissue classes include: air/$CO_2$-filled colon lumen ($x_o$=−1000 Hounsfield units, $\gamma$=50), tag/contrast-filled colon lumen ($x_o$=1000 Hounsfield units, $\gamma$=50), and the edges are a weighed summation of air and contrast voxels with these parameters. Pseudo-code for this calculation for virtual colonoscopy with 36 neighboring voxels is shown in Table 5. In this case, each voxel looks at the neighboring voxels above and below its current y position, but not the voxels at its current y position. This focuses the segmentation calculation so that the air-contrast edge voxels can be determined to complete the colon lumen (i.e., the calculation directs the segmentation neighborhood to follow the naturally pooled contrast which creates a horizontal edge between air and contrast).

TABLE 5

```
for each voxel (x, y, z) do
    sum=0;
    for i = −1 to 1 do
        for j = −2 to 2 do
            for k = −1 to 1 do
                if j NOT EQUAL to 0 then
                {
                    sum += P(w1j(x + i, y + j, z + k));
                    sum += P(w2j(x + i, y + j, z + k));
                };
            end;
        end;
    end;
    P(w3j(x, y, z)) = sum/36;
end
```

More generally, the colon lumen is extracted using a digital subtraction bowel cleansing (DSBC) technique that identifies CT image pixels as: air, contrast material, or pixels at the boundary of air and the contrast material. An accurate 3D model of the colon mucosa may be generated by resetting the greyscale values of the three identified pixel types to a greyscale value of −1,000 Hounsfield units and identifying the lumen-mucosa edge.

Figure 15:
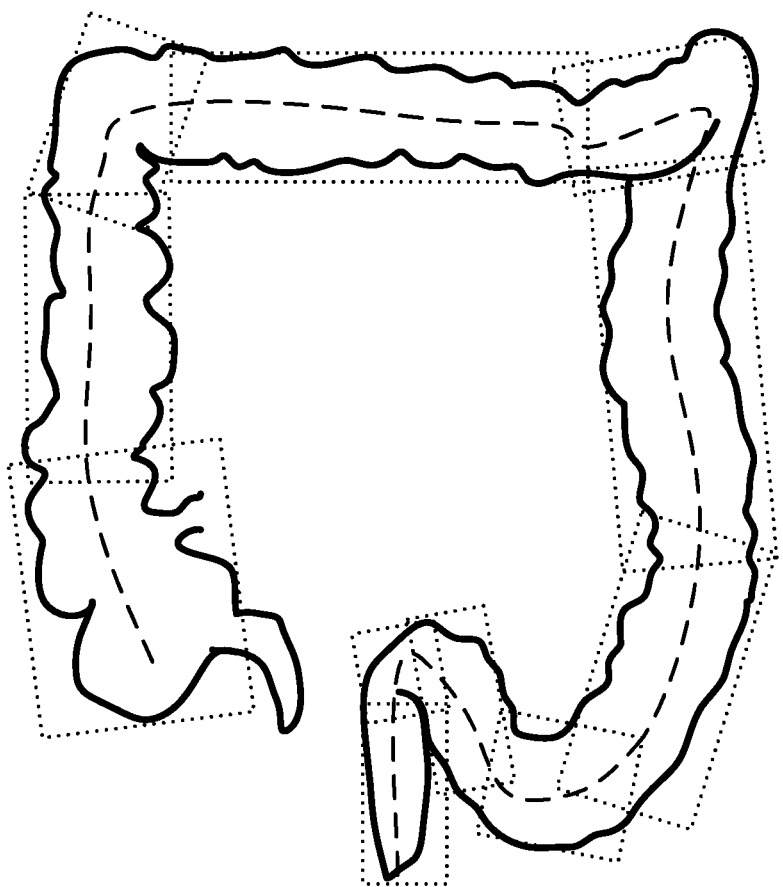
FIG. 15 is a drawing illustrating segmentation in virtual colonoscopy in accordance with an embodiment of the present disclosure.

Furthermore, each colon segment may be enclosed by a bounding box, aligned with the vector connecting the proximal S and the distal D points of the centerline of the colon segment. In order to approximate the geometry of a colon segment, the shape of the bounding boxes may be kept thin (such as an aspect ratio less than 0.25 or 0.3) and may be iteratively subdivided to generate an articulated object model that fits the tortuosity of the patient's colon. As illustrated in FIG. 15, which presents segmentation in virtual colonoscopy, the colon may be divided into at least six standard segments (e.g., the rectum, the sigmoid, the descending colon, the transverse colon, the ascending colon and the cecum). These colon segments may be included in a list of 3D clinical objects of the clinical anatomy for use by the graphics engine.

After segmentation, a high sensitivity and low false-positive rate computer-aided-diagnosis (CAD) technique may be used to: flag polyp candidates by searching through the colon lumen; evaluating if a particular part of the wall is shaped like a polyp (e.g., based on geometric features); and if its neighboring tissue is smooth (e.g., based on texture features).

The graphical system may provide a True 3D-CTC interpretation process that includes: a primary navigation technique that facilitates polyp search via a 3D view of colon segments with a cut plane; detailed polyp evaluation (the clinical targets) using established criteria to identify true polyps; and a problem-solving virtual instrument that provides a combined 2D and a 3D view to reduce false-positive readings (i.e., to correctly identify true polyps).

During colon-segment navigation, the reader or viewer may select a colon segment that is displayed horizontally across its long axis or centerline. With the hand-directed stylus, the reader may place a cut plane to visualize half or more of the colon-segment lumen and may rotate the colon segment on its long axis to bring the rest of the lumen into view. The reader can move on to another colon segment by activating a displayed next or previous button or icon. Moreover, during colon-segment navigation, the reader can bookmark candidate lesions that meet true polyp-morphologic features by selecting them using the stylus and a bookmarking virtual instrument.

During the detailed polyp evaluation, characteristics of a true poly may be used to confirm candidate polys (such as those identified by the CAD technique). Typical characteristics of a true polyp may include: a spherical or hemispherical morphology; smooth borders without angulation; and fixed position for sessile polyps and flat lesions. Polyps may also be correlated with homogeneous soft-tissue density in a 2D image cross-section when viewed using the problem-solving virtual instrument.

In particular, using the problem-solving virtual instrument, bookmarked and CAD polyp candidates may be evaluated in a combined 2D and a 3D view to assess tissue-density homogeneity with morphologic features. Using the hand-directed stylus, the reader can interact with a 2D image projection or cross-section over a 3D view of a polyp or colon segment (with a translucent or transparent surface) to uncover underlying tissue density and neighboring anatomy. Additionally, the reader can integrate lesion motion using correlate supine and prone views, and can focus on polyp candidates using region-of-interest magnification and window-level control. Moreover, the reader can display 2D images with axial and multi-planar reformatted, as well as 3D views including volume rendered images. If the reader points with the stylus to potential lesions, the views being used may be updated for correlation of findings.

True 3D-CTC may provide improved anatomic understanding. Current CTC visualization techniques typically have limitations in representing the complicated 3D relationships present in the colon, which facilitate polyp detection. In order to successfully identify a polyp, radiologists usually must integrate a series of 2D images in their mind and cognitively extract the relevant 3D relationships that define the colon, neighboring anatomy and polyps. In complicated cases, they may have to visually map two or more views of the same data to find appropriate correspondences of one view with another view to produce a match and determine if what they see is a true polyp. Instead, these operations can be provided by the graphical system.

Furthermore, True 3D-CTC can enable immediate colon-lumen identification as open tissue segments with no distortion, and which maintain true or accurate 3D relationships. In particular, True 3D-CTC may provide a better understanding of anatomical shapes because it integrates all three dimensions and corresponding depth cues in a single view.

True 3D-CTC may also provide increased polyp sensitivity. Reader perceptual error is a reason for false-negatives. Ideally, polyps are visible as abnormal structures that protrude the colon wall. However, when polyps are less conspicuous, radiologists typically report that: polyps appear flat; polyp edges are not prominent (e.g., not well defined); polyps are difficult to distinguish from a normal fold; polyps look like noise or a normal bump on the colonic surface; and/or the polyp looks like stool. Studies have determined that polyp height is a major determinant of visual conspicuity.

Viewing polyp images with True 3D-CTC may be better than analyzing monoscopic 3D-rendered images, because the visual features that define a polyp (such as its shape, size, height and edges) can be magnified as a function of image perspective and parallax. In particular, strong parallax can enhance the visual elevation of polyps and the visual prominence of edges in colon structures, and can improve the contextual features of colon folds.

True 3D-CTC can be used to reduce interpretation time. The colon-segment navigation technique described above can eliminate anterograde and retrograde endoluminal navigation, thereby decreasing interpretation times and reducing reader tracking of the colon when there are redundant segments, aberrant anatomy, or if collapsed segments are present. The colon-segment navigation technique also has the potential to simplify reader decisions by displaying undistorted colon segments that preemptively remind readers of particular colon-segment normal and abnormal anatomy.

Additionally, True 3D-CTC may increase reader tolerance to image noise. Low-dose CTC imaging techniques are now standard of care. However, overall image quality is reduced as the radiation dose decreases (e.g., there is reduced soft-tissue contrast and higher image noise). In particular, in 3D endoluminal images, artifacts like mucosal nodularity and endoluminal floaters can become more prominent. While techniques such as adaptive statistical iterative reconstruction (ASIR) can significantly reduce noise in low-dose images, imaging artifacts can persist in 3D reconstructions. Viewing low-dose polyp images with True 3D-CTC may offer improved performance, because it enables readers to see through clutter in the foreground or background, and makes it possible to focus at different depth levels, potentially increasing the reader's tolerance to image noise in low-dose CTC.

Combining True 3D-CTC with CAD can improve true-positive and false-positive discrimination. In general, conventional CTC combined with CAD is associated with high false-positive rates, leaving readers the hard task of visually mapping 2D and 3D views to discriminate true from false-positives. True 3D-CTC plus CAD can reduce true-positive and false-positive discrimination times because the problem-solving virtual instrument can enable the assessment of lesion tissue-density homogeneity with polyp morphologic features in a combined 2D and a3D view.

Finally, controlling CAD polyp candidates and any bookmarked polyp candidates with a hand-directed stylus offloads spatial cognition onto the reader's perceptual motor system, instead of performing a mental rotation or an imagined perspective shift, thereby reducing the cognitive intensity of CTC interpretation.

For these reasons, True 3D is expected to provide a significant improvement in CTC. This was borne out in preliminary benchmark testing. In particular, using a public CTC dataset, True 3D increased the detection rate for a flat lesion greater than 6 mm by 20%. Such improvements in CTC accuracy may be important factor for patient screening compliance and cost-effectiveness, as well as a key contributor of patients' preference of CTC over ordinary colonoscopy.

Another diagnostic application of True 3D is in mammography (i.e., the volumetric interpretation of breast images based on mass and context tissue). In particular, True 3D may be used to: landmark fibro-glandular tissue, veins and fat; determine prior volume and size; determine the path of calcification clusters; and delineate masses and tumors.

Another diagnostic application of True 3D is in diagnosing labrum tears in orthopedics. The labrum is a fibro cartilaginous rim attached around the margin of the glenoid cavity in the shoulder blade. When it tears (for example, due to strenuous exercise or exertion), the patient feels pain. A tissue-class segmentation technique similar to that described previously can be used to identify bones (tissue class 1), soft tissue (tissue class 2) and cartilage (tissue class 3), thereby creating an edge between bones in a joint. After this segmentation, each tissue class can provide a mask for volume rendering or a surface, and can be decomposed in order to extract the labrum.

Yet another diagnostic application of True 3D is in lung-cancer screening, in which nodules grow in a patient's airways. Detecting such nodules can be difficult because of the irregular structure of the bronchi as it spreads across ten pulmonary segments. Once again, the tissue-class segmentation technique may be used to identify air (tissue class 1) and the lumen of the bronchus (tissue class 2). The placement of the bronchi segments enables a structured-review methodology so that physicians can better identify nodules, their size and shape, as well as precisely locate the nodules in the pulmonary segments.

As described further below with reference to FIG. 19, true 3D may also be used for surgical planning and/or to provide situational awareness and assist or guide a surgeon during a surgical procedure (such as a minimally invasive surgical procedure) using preoperative and/or intraoperative images. In particular, using graphical system 100 (FIG. 1) and/or computer system 600 (FIG. 6) the surgeon (or a physician) may visualize patient specific anatomy that has been identified as part of the preoperative plan at its patient specific location through the patient's body and plan out a series of tasks or operations they will perform on a patient during a planned surgical procedure (i.e., to determine a surgical plan). True 3D may allow the surgeon to view the 3D environment in the patient (including organs and landmarks in the context of the patient's anatomy) as the planned surgical procedure progresses. This may allow the surgeon to visualize the planned surgical procedure and to interact with the 3D stereoscopic images (which may include haptic interaction with a virtual instrument as a surgical tool) so that the surgeon can determine an efficient manner in which to perform the planned surgical procedure. The resulting set of 3D stereoscopic images (including image parallax, motion parallax, prehension and/or stereopsis scaling) may be saved by the surgeon for subsequent viewing before and/or during the surgical procedure.

Furthermore, the set of 3D stereoscopic images may be dynamically updated during the surgical procedure if the surgeon deviates from the predefined surgical plan. In particular, the set of 3D stereoscopic images may be displayed on a 3D display (such as a monitor, an augmented-reality headset, a retina projector, projected onto the patient, etc.) in the operating room during the surgical procedure. For example, 3D stereoscopic images may be displayed on the patient, so that the surgeon can see 3D patient-specific tissue and organs through the patient's skin and/or the surgical gown or cloth that covers the patient. Computer system 600 (FIG. 6) may step through the set of 3D stereoscopic images as the surgical procedure progresses, e.g., based on user input via a user interface or voice commands, or based on information that specifies the surgeon's actions or location in patient's anatomy. For example, the information may include dynamic tracking of the surgeon and/or one or more of the surgeon's surgical tools (such as a scalpel), using: a local positioning system (such as a 3D local positioning system that tracks the position of one or more surgical tools in the patient, such as relative to one or more anatomical landmarks in the patient), image processing of images acquired in the operating room, etc. For example, the local positioning system may include: Global Positioning information, triangulation and/or trilateration based on local positioning landmarks (e.g., via a wireless network, such as Wi-Fi or a cellular-telephone network), laser interferometry, etc. If the surgeon intentionally or unintentionally deviates from the predefined surgical plan (e.g., using on-the-fly or dynamic analysis of the location of a surgical tool relative to the predefined surgical plan), computer system 600 (FIG. 6) may update or revise the displayed 3D stereoscopic images. The revised 3D stereoscopic images may reflect or indicate: that a deviation from the predefined surgical plan has occurred (e.g., via visual, auditory and/or sensory feedback), the current location (relative to the patient's anatomy), and/or how to correct the deviation so that the surgical procedure follows the predefined surgical plan.

Before, during and/or at the end of the surgical procedure, the surgical plan, the locations of the surgical instruments and the progression of the surgical procedure, and the outcome may be saved in a computer-readable data structure for subsequent analysis and/or use.

Methods

Figure 16:
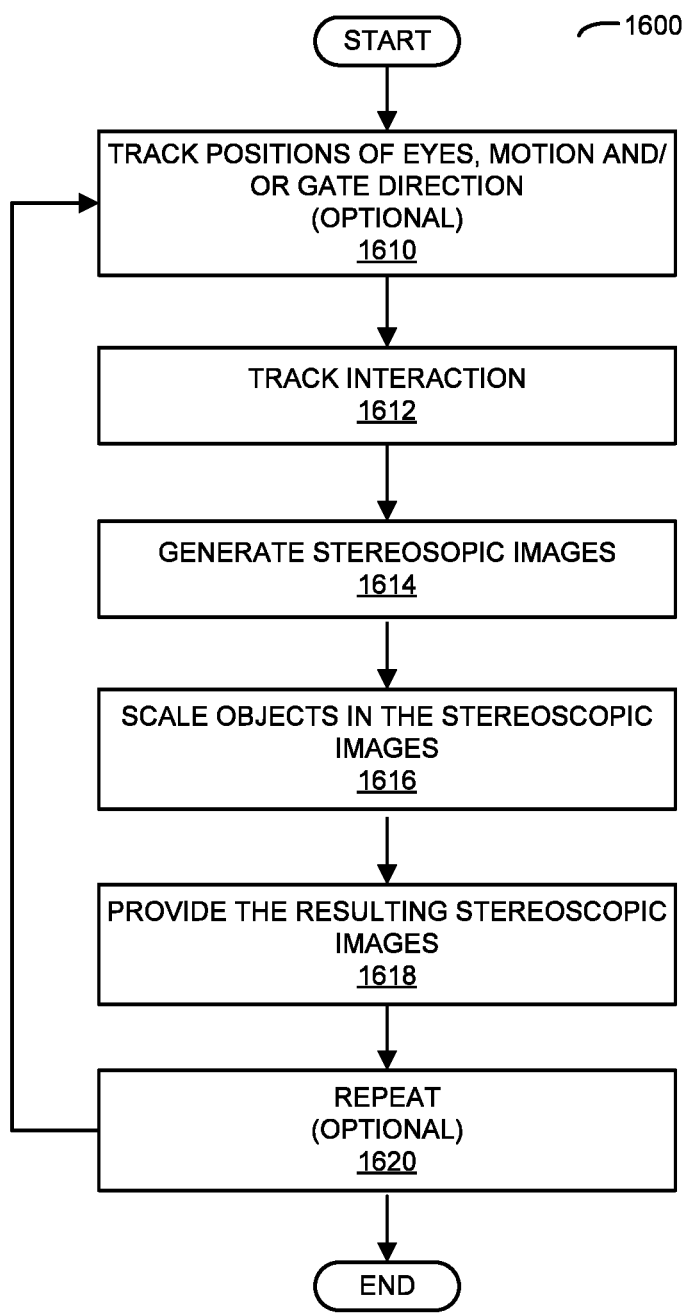
FIG. 16 is a flow diagram illustrating a method for providing stereoscopic images in accordance with an embodiment of the present disclosure.

FIG. 16 presents a flow diagram illustrating a method 1600 for providing stereoscopic images, which may be performed by graphical system 100 (FIG. 1) and, more generally, a computer system. During operation, the computer system generates the stereoscopic images (operation 1614) at a location corresponding to a viewing plane based on data having a discrete spatial resolution, where the stereoscopic images include image parallax. Then, the computer system scales objects in the stereoscopic images (operation 1616) so that depth acuity associated with the image parallax is increased, where the scaling (or stereopsis scaling) is based on the spatial resolution and a viewing geometry associated with a display. For example, the objects may be scaled prior to the start of rendering. Next, the computer system provides the resulting stereoscopic images (operation 1618) to the display. For example, the computer system may render and provide the stereoscopic images.

Note that the spatial resolution may be associated with a voxel size in the data, along a direction between images in the data and/or any direction of discrete sampling.

Moreover, the viewing plane may correspond to the display. In some embodiments, the computer system optionally tracks positions of eyes (operation 1610) of an individual that views the stereoscopic images on the display. The stereoscopic images may be generated based on the tracked positions of the eyes of the individual. Furthermore, the computer system may optionally track motion (operation 1610) of the individual, and may optionally re-generate the stereoscopic images based on the tracked motion of the individual (operation 1618) so that the stereoscopic images include motion parallax. Additionally, the computer system may optionally track interaction (operation 1612) of the individual with information in the displayed stereoscopic images, and may optionally re-generate the stereoscopic images based on the tracked interaction so that the stereoscopic images include prehension by optionally repeating (operation 1620) one or more operations in method 1600. For example, the individual may interact with the information using one or more interaction tools. Thus, when generating the stereoscopic images (operation 1614) or preparing the stereoscopic images, information from optionally tracked motion (operation 1610) and/or the optionally tracked interaction may be used to generate or revise the view and projection matrices.

Note that the stereoscopic images may include a first image to be viewed by a left eye of the individual and a second image to be viewed by a right eye of the individual. Moreover, the viewing geometry may include a distance from the display of the individual and/or a focal point of the individual.

In some embodiments, generating the stereoscopic images is based on: where the information in the stereoscopic images is located relative to the eyes of the individual that views the stereoscopic images on the display; and a first frustum for one of the eyes of the individual and a second frustum for another of the eyes of the individual that specify what the eyes of the individual observe when viewing the stereoscopic images on the display. Furthermore, generating the stereoscopic images may involve: adding monoscopic depth cues to the stereoscopic images; and rendering the stereoscopic images.

In some embodiments, the computer system optionally tracks a gaze direction (operation 1610) of the individual that views the stereoscopic images on the display. Moreover, an intensity of a given voxel in a given one of the stereoscopic images may be based on a transfer function that specifies a transparency of the given voxel and the gaze direction so that the stereoscopic images include foveated imaging.

Figure 17:
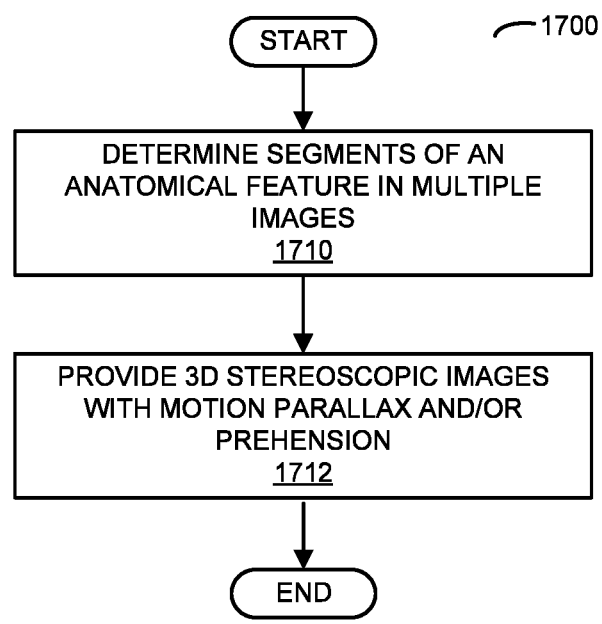
FIG. 17 is a flow diagram illustrating a method for determining segments of an anatomical feature in multiple images in accordance with an embodiment of the present disclosure.

FIG. 17 presents a flow diagram illustrating a method 1700 for determining segments of an anatomical feature in multiple images, which is sometimes referred to as 'segment navigation,' and which may be performed by graphical system 100 (FIG. 1) and, more generally, a computer system. During operation, the computer system determines segments of an anatomical feature in multiple images (operation 1710). These segments may describe the anatomical feature using a hierarchical arrangement of nodes and branches. Furthermore, the segments may have aspect ratios less than a pre-determined value. Using the segments, the computer system may provide 3D stereoscopic images with motion parallax and/or prehension (operation 1712). For example, the segments may facilitate: more compact storage of information corresponding to the anatomical feature, fast extraction of regions of interest by the computer system, and faster rending of the 3D stereoscopic images by the computer system.

Figure 18:
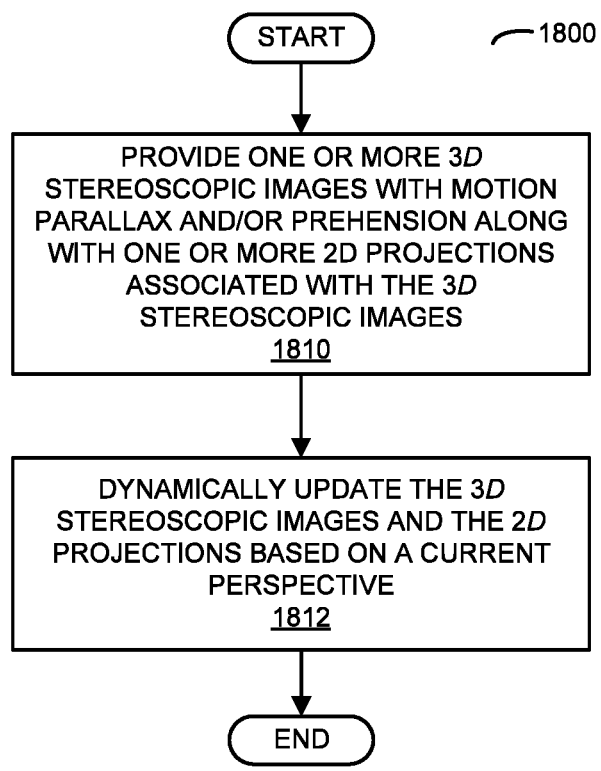
FIG. 18 is a flow diagram illustrating a method for providing 3D stereoscopic images and associated 2D projections in accordance with an embodiment of the present disclosure.

FIG. 18 presents a flow diagram illustrating a method 1800 for providing 3D stereoscopic images and associated 2D projections, which may be performed by graphical system 100 (FIG. 1) and, more generally, a computer system. During operation, the computer system provides one or more 3D stereoscopic images with motion parallax and/or prehension along with one or more 2D projections (or cross-sectional views) associated with the 3D stereoscopic images (operation 1810). The 3D stereoscopic images and the 2D projections may be displayed side by side on a common display. Moreover, as the user interacts with the 3D stereoscopic images and/or the one or more 2D projections and changes their viewing perspective, the computer system may dynamically update the 3D stereoscopic images and the 2D projections based on the current perspective (operation 1812). In some embodiments, note that the 2D projections are always presented along a perspective direction perpendicular to the user so that motion parallax is registered in the 2D projections.

Figure 19:
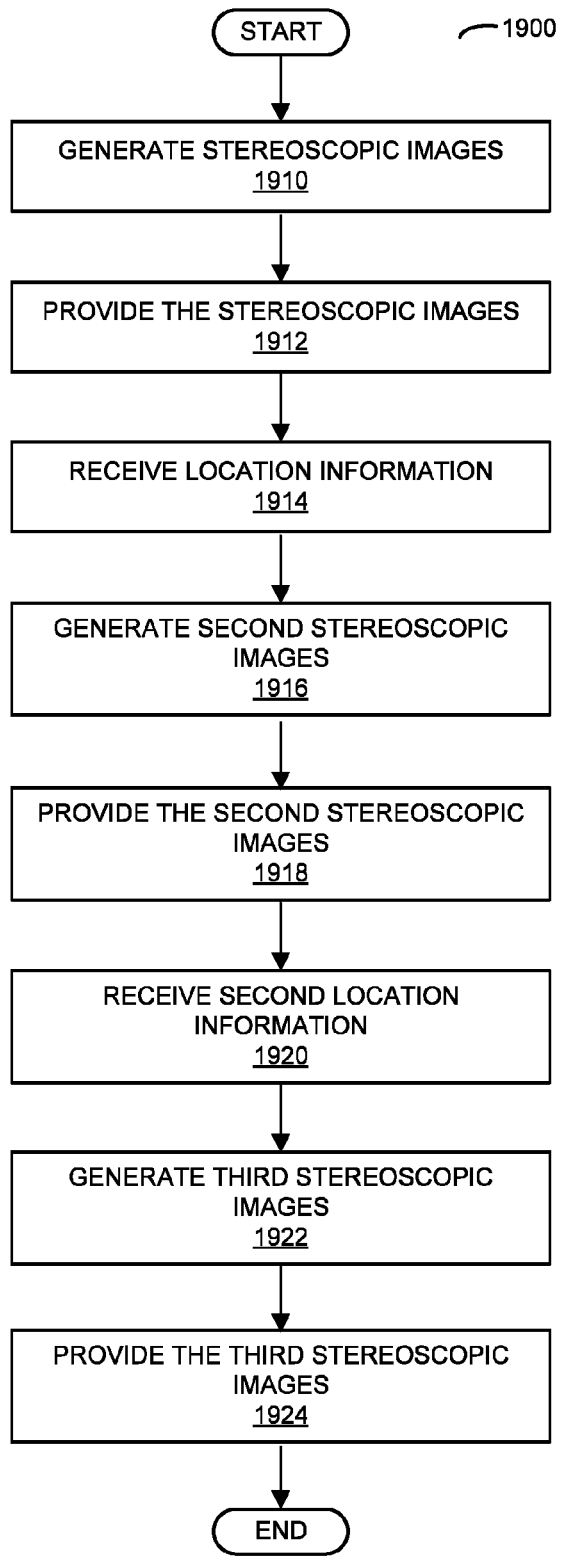
FIG. 19 is flow diagram illustrating a method for providing situational awareness and feedback during a surgical procedure in accordance with an embodiment of the present disclosure.

FIG. 19 presents a flow diagram illustrating a method 1900 for providing situational awareness and feedback during a surgical procedure, which may be performed by graphical system 100 (FIG. 1) and, more generally, a computer system. During operation, the computer system generates stereoscopic images (operation 1910) at a first 3-dimensional (3D) location in an individual, where the stereoscopic images include image parallax, and where the stereoscopic images correspond to a first viewing plane and are based on data having a discrete spatial resolution and a predefined surgical plan for the individual from preoperative and/or intraoperative images. Then, the computer system provides the stereoscopic images (operation 1912) to a display. Moreover, the computer system receives location information (operation 1914) of one or more surgical tools as they are being advanced or positioned in the patient. Then, the computer system generates second stereoscopic images (operation 1916) at a second 3D location in the individual, where the second stereoscopic images include image parallax and motion parallax relative to the stereoscopic images, and where the second stereoscopic images correspond to a second viewing plane and are based on the data having the discrete spatial resolution and the predefined surgical plan for the individual. Then, the computer system provides the second stereoscopic images (operation 1918) to the display. Next, the computer system receives second location information (operation 1920) that indicates a deviation from the predefined surgical plan during the surgical procedure. Furthermore, the computer system generates third stereoscopic images (operation 1922) at a third 3D location in the individual, where the third stereoscopic images include image parallax and motion parallax relative to the second stereoscopic images, and where the third stereoscopic images correspond to a third viewing plane and are based on the data having the discrete spatial resolution and the predefined surgical plan for the individual. Additionally, the computer system provides the third stereoscopic images (operation 1924) to the display.

Note that the location information and/or the second location information may track the progression of treatment across multiple interventions (radiation oncology, surgical, etc.). For example, the tracking of the position of surgical tools may be extended to track the location of where treatment has been applied across many surgeries (such as in radiation oncology) to determine how a tumor may be shrinking, etc, Moreover, the second viewing plane and the third viewing plane may overlap with the first viewing plane to provide the stereoscopic images in a common frame of reference. For example, the second viewing plane may be registered with the third viewing plane. In some embodiments, the second viewing plane and the third viewing plane are the same as the first viewing plane.

In some embodiments of methods 1600, 1700, 1800 and/or 1900 there may be additional or fewer operations. Moreover, the order of the operations may be changed, and/or two or more operations may be combined into a single operation.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A computer-implemented method for providing situational awareness and feedback during a surgical procedure, wherein the method comprises:
    using the computer system, generating stereoscopic images from a preoperative image located at a first 3-dimensional (3D) location in an individual, wherein the stereoscopic images include image parallax, and wherein the stereoscopic images correspond to a first viewing plane and are based on data having a discrete spatial resolution and a predefined surgical plan for the individual;
    providing the stereoscopic images to a display;
    receiving location information of a surgical tool relative to the individual;
    generating second stereoscopic images from a preoperative image located at a second 3D location in the individual, wherein the second stereoscopic images include image parallax motion parallax relative to the stereoscopic images, and wherein the second stereoscopic images correspond to a second viewing plane and are based on the data and the predefined surgical plan for the individual;
    providing the second stereoscopic images to the display;
    receiving second location information that indicates a deviation from the predefined surgical plan during the surgical procedure;
    generating third stereoscopic images at a third 3D location in the individual, wherein the third stereoscopic images include image parallax and motion parallax relative to the second stereoscopic images, and wherein the third stereoscopic images correspond to a third viewing plane and are based on the data and the predefined surgical plan for the individual; and
    providing the third stereoscopic images to the display.

2. The method of claim 1, wherein the third stereoscopic images indicate that the deviation has occurred.

3. The method of claim 1, wherein the third stereoscopic images update the location of the surgical tool and the predefined surgical plan.

4. The method of claim 1, wherein the third stereoscopic images indicate how to return to the predefined surgical plan.

5. The method of claim 1, wherein the third stereoscopic images include intraoperative images in combination with the preoperative images and providing the stereoscopic images involves displaying the stereoscopic images on the display.

6. The method of claim 1, wherein the location information and/or the second location information track the position of the one or more surgical tools in the individual based on information from a 3D local positioning system.

7. The method of claim 1, wherein at least one of the location information and the second location information track the progression of treatment across multiple interventions.

8. The method of claim 1, wherein the second viewing plane and the third viewing plane overlap with the first viewing plane to provide the stereoscopic images in a common frame of reference.

9. A computer-program product for use in conjunction with a computer system, the computer-program product comprising a non-transitory computer-readable storage medium and a computer-program mechanism embedded therein, to provide situational awareness and feedback during a surgical procedure, the computer-program mechanism including:
    instructions for generating stereoscopic images from a preoperative image located at a first 3-dimensional (3D) location in an individual, wherein the stereoscopic images include image parallax, and wherein the stereoscopic images correspond to a first viewing plane and are based on data having a discrete spatial resolution and a predefined surgical plan for the individual;
    instructions for providing the stereoscopic images to a display;
    instructions for receiving location information of a surgical tool relative to the individual;
    instructions for generating second stereoscopic images from a preoperative image located at a second 3D location in the individual, wherein the second stereoscopic images include image parallax motion parallax relative to the stereoscopic images, and wherein the second stereoscopic images correspond to a second viewing plane and are based on the data and the predefined surgical plan for the individual;
    instructions for providing the second stereoscopic images to the display;
    instructions for receiving second location information that indicates a deviation from the predefined surgical plan during the surgical procedure;
    instructions for generating third stereoscopic images at a third 3D location in the individual, wherein the third stereoscopic images include image parallax and motion parallax relative to the second stereoscopic images, and wherein the third stereoscopic images correspond to a third viewing plane and are based on the data and the predefined surgical plan for the individual; and
    instructions for providing the third stereoscopic images to the display.

10. The computer-program product of claim 9, wherein the third stereoscopic images indicate that the deviation has occurred.

11. The computer-program product of claim 9, wherein the third stereoscopic images update to the predefined surgical plan.

12. The computer-program product of claim 9, wherein the third stereoscopic images indicate how to return to the predefined surgical plan.

13. The computer-program product of claim 9, wherein the instructions for providing the stereoscopic images, the instructions for providing the second stereoscopic images and the instructions for instructions for providing the third stereoscopic images include, respectively, displaying the stereoscopic images, the second stereoscopic images and the third stereoscopic images on the display.

14. The computer-program product of claim 9, wherein the location information and/or the second location information track the position of the one or more surgical tools in the individual based on information from a 3D local positioning system.

15. A computer system, comprising:
a processor; and
memory, wherein the memory stores a program module, and wherein the program module is configured to be executed by the processor to provide situational awareness and feedback during a surgical procedure, the program module including:
  instructions for generating stereoscopic images from a preoperative image located at a first 3-dimensional (3D) location in an individual, wherein the stereoscopic images include image parallax, and wherein the stereoscopic images correspond to a first viewing plane and are based on data having a discrete spatial resolution and a predefined surgical plan for the individual;
  instructions for providing the stereoscopic images to a display;
  instructions for receiving location information of a surgical tool relative to the individual;
  instructions for generating second stereoscopic images from a preoperative image located at a second 3D location in the individual, wherein the second stereoscopic images include image parallax motion parallax relative to the stereoscopic images, and wherein the second stereoscopic images correspond to a second viewing plane and are based on the data and the predefined surgical plan for the individual;
  instructions for providing the second stereoscopic images to the display;
  instructions for receiving second location information that indicates a deviation from the predefined surgical plan during the surgical procedure;
  instructions for generating third stereoscopic images at a third 3D location in the individual, wherein the third stereoscopic images include image parallax and motion parallax relative to the second stereoscopic images, and wherein the third stereoscopic images correspond to a third viewing plane and are based on the data and the predefined surgical plan for the individual; and
  instructions for providing the third stereoscopic images to the display.

16. The computer system of claim 15, wherein the third stereoscopic images indicate that the deviation has occurred.

17. The computer system of claim 15, wherein the third stereoscopic images update to the predefined surgical plan.

18. The computer system of claim 15, wherein the third stereoscopic images indicate how to return to the predefined surgical plan.

19. The computer system of claim 15, wherein the computer system includes a display; and
wherein the instructions for providing the stereoscopic images, the instructions for providing the second stereoscopic images, and the instructions for providing the third stereoscopic images include, respectively, displaying the stereoscopic images, the second stereoscopic images, and the third stereoscopic images on the display.

20. The computer system of claim 15, wherein the location information and/or the second location information track the position of the one or more surgical tools in the individual based on information from a 3D local positioning system.

* * * * *